(12) United States Patent
Yatscoff et al.

(10) Patent No.: US 6,686,454 B1
(45) Date of Patent: Feb. 3, 2004

(54) ANTIBODIES TO SPECIFIC REGIONS OF CYCLOSPORINE RELATED COMPOUNDS

(75) Inventors: Randall W. Yatscoff, Alberta (CA); Andrew J. Malcolm, Alberta (CA); S. Selvaraj Naicker, Alberta (CA)

(73) Assignee: Isotechnika, Inc., Edmonton (CA)

( * ) Notice: Subject to any disclaimer, the term of this patent is extended or adjusted under 35 U.S.C. 154(b) by 0 days.

(21) Appl. No.: 09/390,280

(22) Filed: Sep. 3, 1999

Related U.S. Application Data

(63) Continuation-in-part of application No. 09/168,885, filed on Oct. 9, 1998, now abandoned.

(51) Int. Cl.[7] .................. C07K 16/00; G01N 33/53; C12N 5/06; A61K 39/395

(52) U.S. Cl. ............... 530/388.9; 530/388.1; 530/387.9; 435/326; 435/975; 424/175.1

(58) Field of Search .................. 530/388.1, 317, 530/387.1, 388.9, 387.9, 806, 807; 435/975, 452, 326; 436/815; 426/175.1

(56) References Cited

U.S. PATENT DOCUMENTS

| | | | |
|---|---|---|---|
| 4,914,188 A | 4/1990 | Dumont et al. | |
| 5,169,773 A | 12/1992 | Rosenthaler et al. | |
| 5,604,092 A | 2/1997 | Erlanger et al. | |
| 6,054,303 A | 4/2000 | Davallian et al. | |
| 6,106,828 A | 8/2000 | Bisgard-Frantzen et al. | 424/94.1 |
| 6,190,873 B1 * | 2/2001 | Davalian et al. | 435/7.93 |
| 6,309,646 B1 * | 10/2001 | Lees | 424/195.11 |

FOREIGN PATENT DOCUMENTS

| | | |
|---|---|---|
| EP | 0 283 801 | 9/1988 |
| EP | 0 487 289 | 11/1991 |
| WO | WO8602080 | 4/1986 |
| WO | WO9006763 | 6/1990 |
| WO | WO 93/01498 * | 1/1993 |
| WO | WO9845333 | 10/1998 |

OTHER PUBLICATIONS

Yatscoff et al. Clin. Chem. 36: 1969–1973, 1990.*

Lensmeyer et al. Clin. Chem. 36:119 123, 1990.*

Ye, L., et al., "Competitive Immunoassay for Cyclosporine Using Capillary Electrophoresis with Laser Induced Fluorescence Polarization Detection," *Journal of Chromatography. B, Biomedical Sciences and Applications*, 714 (1) 59–67 (Aug. 1998).

Chen, P., et al., "A Sensitive Enzyme Immunoassay for Cyclosporin A Using Antibodies Generated Against a Novel Hapten," *Research Communications in Molecular Pathology and Pharmacology*, 88 (3) 317–26 (Jun. 1995).

Somayaji, Vijayalkshmi V., et al., "Preparation and Protein Conjugation of a Divinyl Sulfone–Derivatized Bifunctional Chelating Agent," *Cancer Biother. Radiopharm*, 11(6), 405–414 (1996).

Cacalano, N.A., et al., "Novel Monoclonal Antibodies to Cyclosporine A: Characterization and Epitope Mapping with Cyclosporine Analogs and Cyclophilin," *Molecular Immunology* 29: 107–118 (1992).

Copeland, K.R., et al., "The Isolation, Structural Characterization, and Immunosuppressive Activity of Cyclosporin G ($Nva^2$–Cyclosporine) Metabolites," *Therapeutic Drug Monitoring* 13: 281–288 (1991).

Quesniaux, V., et al., "An Enzyme Immunoassay for the Screening of Monoclonal Antibodies to Cyclosporin," *Immunology Letter* 9: 99–104 (1985).

Quesniauz, V., et al., "Fine Specificity and Cross–Reactivity of Monoclonal Antibodies to Cyclosporine," *Molecular Immunology* 24: 1159–1168 (1987).

Quesniaux, V., et al., "Monoclonal Antibody Technology for Cyclosporine Monitoring," *Clinical Biochemistry* 24:37–42 (1991).

Ed Harlow et al., "Antibodies A Laboratory Manual", pp. 341 and 324, Cold Spring Harbor Laboratory (1998), Cold Spring Harbor Laboratory Press, New York, USA.

P. Chen et al., (Abstract Only) "A Sensitive Enzyme Immunoassay for Cyclosporin A Using Antibodies Generated against a Novel Hapten", Res Commun Mol Pathol Pharmacol (1995) Jun.;88(3)317–26.

(List continued on next page.)

*Primary Examiner*—S. Devi
(74) *Attorney, Agent, or Firm*—Burns, Doane, Swecker & Mathis, L.L.P.

(57) ABSTRACT

This invention relates to the production of polyclonal and monoclonal antibodies to specific regions of cyclosporine (CSA) and/or CSA metabolites/derivatives. The reactivity of these polyclonal and monoclonal antibodies make them particularly useful for immunoassays for therapeutic drug monitoring (TDM). These immunoassays or TDM kits may include polyclonal or monoclonal antibodies to specific sites of CSA and/or CSA metabolites. These kits may also include various combinations of polyclonal antibodies, polyclonal and monoclonal antibodies or a panel of monoclonal antibodies. Cyclosporine or CSA metabolite conjugate immunogens are prepared for the immunization of a host animal to produce antibodies directed against specific regions of the CSA or CSA metabolite molecule. By determining the specific binding region of a particular antibody, immunoassays which are capable of distinguishing between the parent molecule, active metabolites, inactive metabolites and other structurally similar immunosuppressant compounds are developed. The use of divinyl sulfone (DVS) as the linker arm molecule for forming cyclosporine and cyclosporine metabolite protein conjugate immunogens is described.

3 Claims, 9 Drawing Sheets

OTHER PUBLICATIONS

Shan S. Wong, "Chemistry of Protein Conjugation and Cross–Linking," Chapter 4, "Homobifunctional Cross–Linking Reagents," pp. 75–145 (1993), CRC Press Ltd.

Shan S. Wong, "Chemistry of Protein Conjugation and Cross–Linking," Chapter 5, "Heterobifunctional Cross–Linkers," pp. 147–194 (1993), CRC Press Ltd.

R. K. Crossland, et al., "Sulfonate Leaving Groups, Structure and Reactivity. 2,2,2–Trifluoroethanesulfonate," Journal of the American Chemical Society, vol. 93, No. 17, pp. 4217–4219 (1971).

J. Milton Harris, et al., "Synthesis and Characterization of Poly(ethylene Glycol) Derivatives," Journal of Polymer Science, Polymer Chemistry Edition, vol. 22, pp. 341–352 (1984).

J. Milton Harris, "Laboratory Synthesis of Polyethylene Glycol Derivatives," JMS–Rev. Macromol. Chem. Phys., C25(3), pp. 325–373 (1985).

Tae H. Ji, et al., "Bifunctional Reagents," *Methods of Enzymology*, vol. 91, pp. 580–609 (1983) Academic Press, Inc.

Gary E. Means, et al., "Chemical Modifications of Proteins: History and Applications," Bioconjugate Chem. 1, pp. 2–12 (1990).

Kurt Nilsson, et al., "Immobilization of Ligands with Organic Sulfonyl Chlorides," *Methods in Enzymology*, vol. 104, pp. 56–96 (1984) Academic Press, Inc.

Kurt Nilsson, et al., "Tresyl Chloride–Activated Supports for Enzyme Immobilization," *Methods in Enzymology*, vol. 135, pp 65–78 (1987) Academic Press, Inc.

William H. Scouten, et al., "Colored Sulfonyl Chloride as an Activating Agent for Hydroxylic Matrices," *Methods in Enzymology*, vol. 135, pp. 79–84 (1987) Academic Press, Inc.

\* cited by examiner

Figure 3: Inhibition ELISA of AM19-9-5A6 MoAb Showing Selectivity for AM1

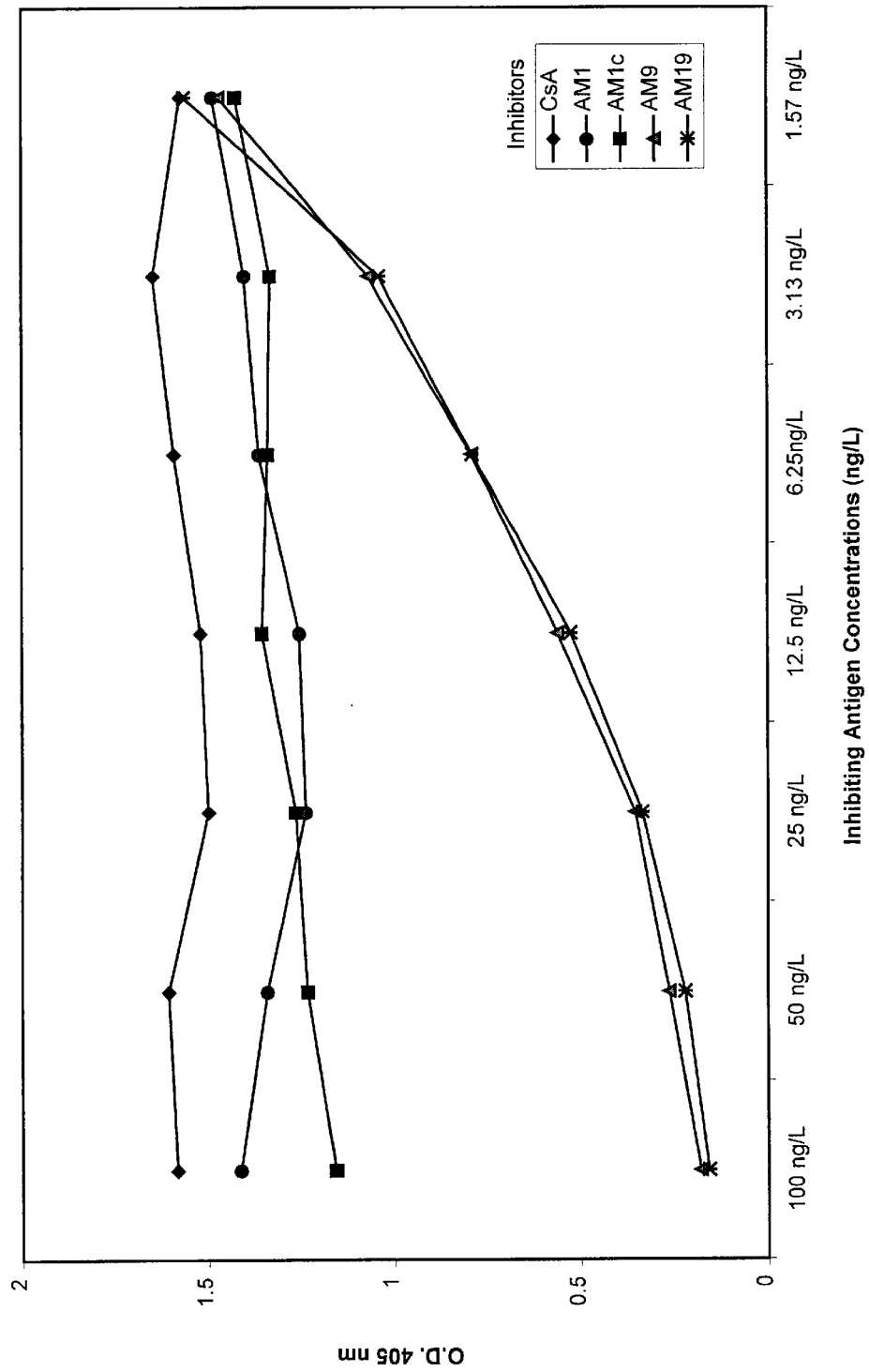
Figure 4: Inhibition ELISA of AM9-1-7D2 MoAb Showing Selectivity for AM9

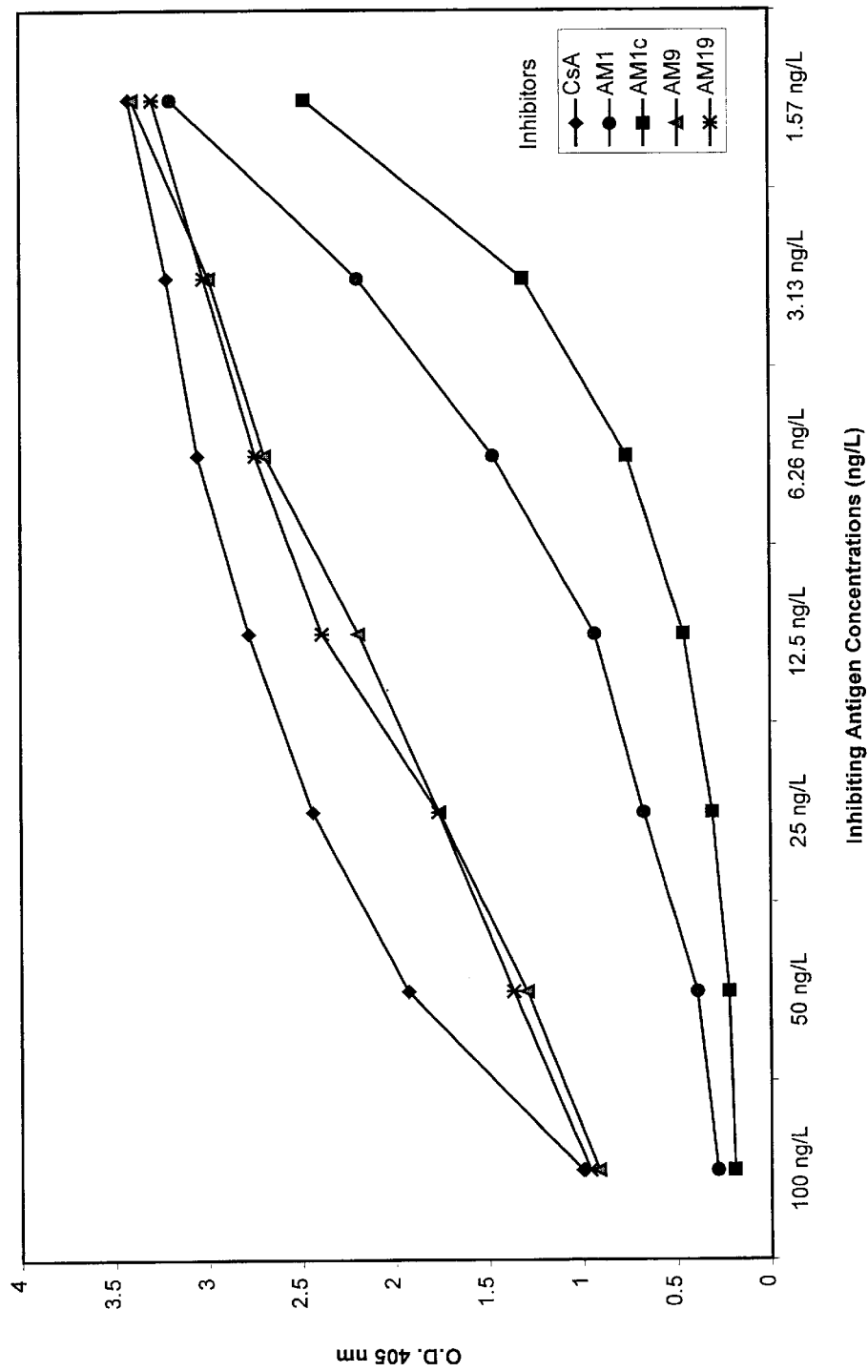
Figure 5: Inhibition ELISA of AM19-1-7E12 MoAb Showing Selectivity for AM1 and AM1c

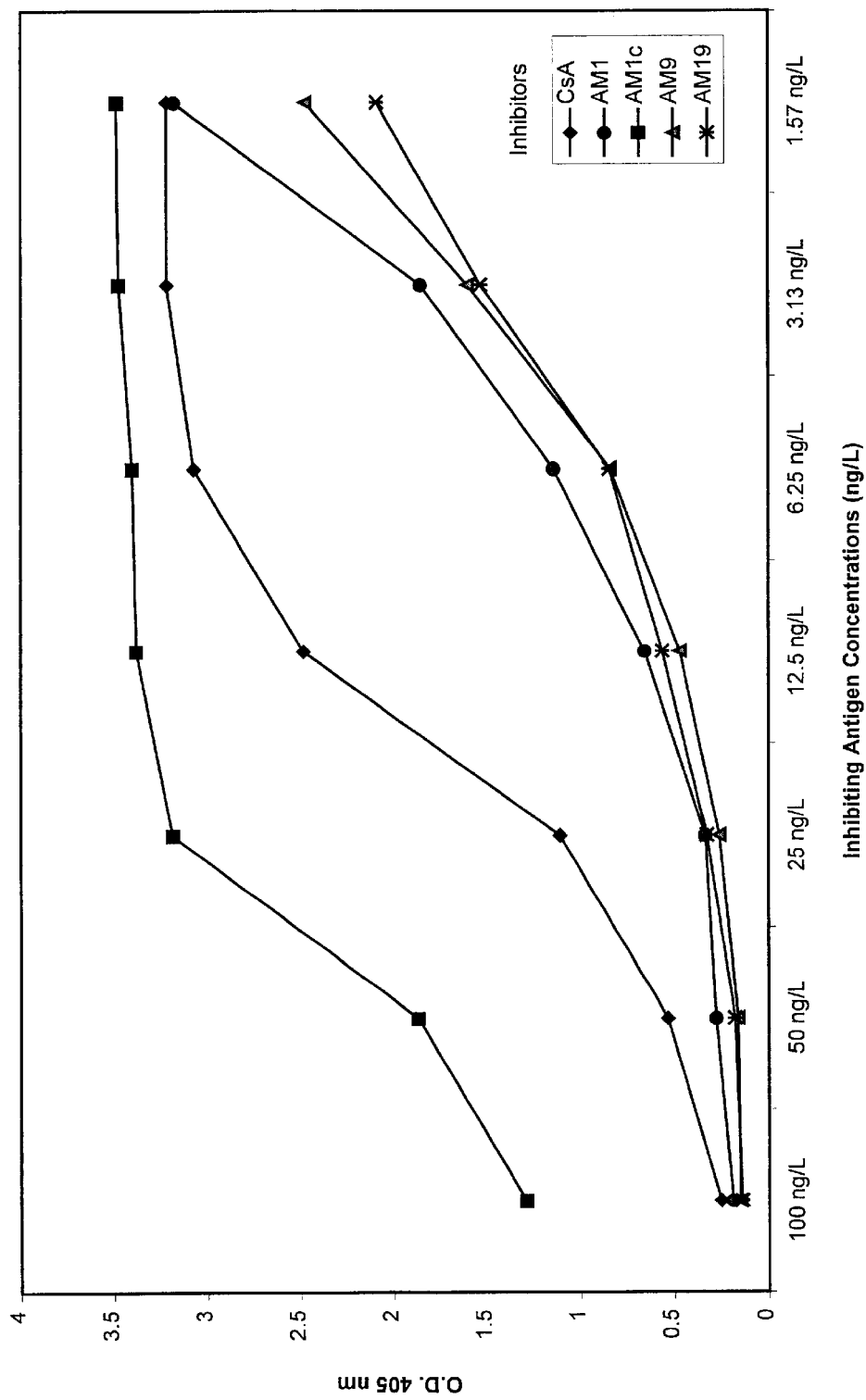

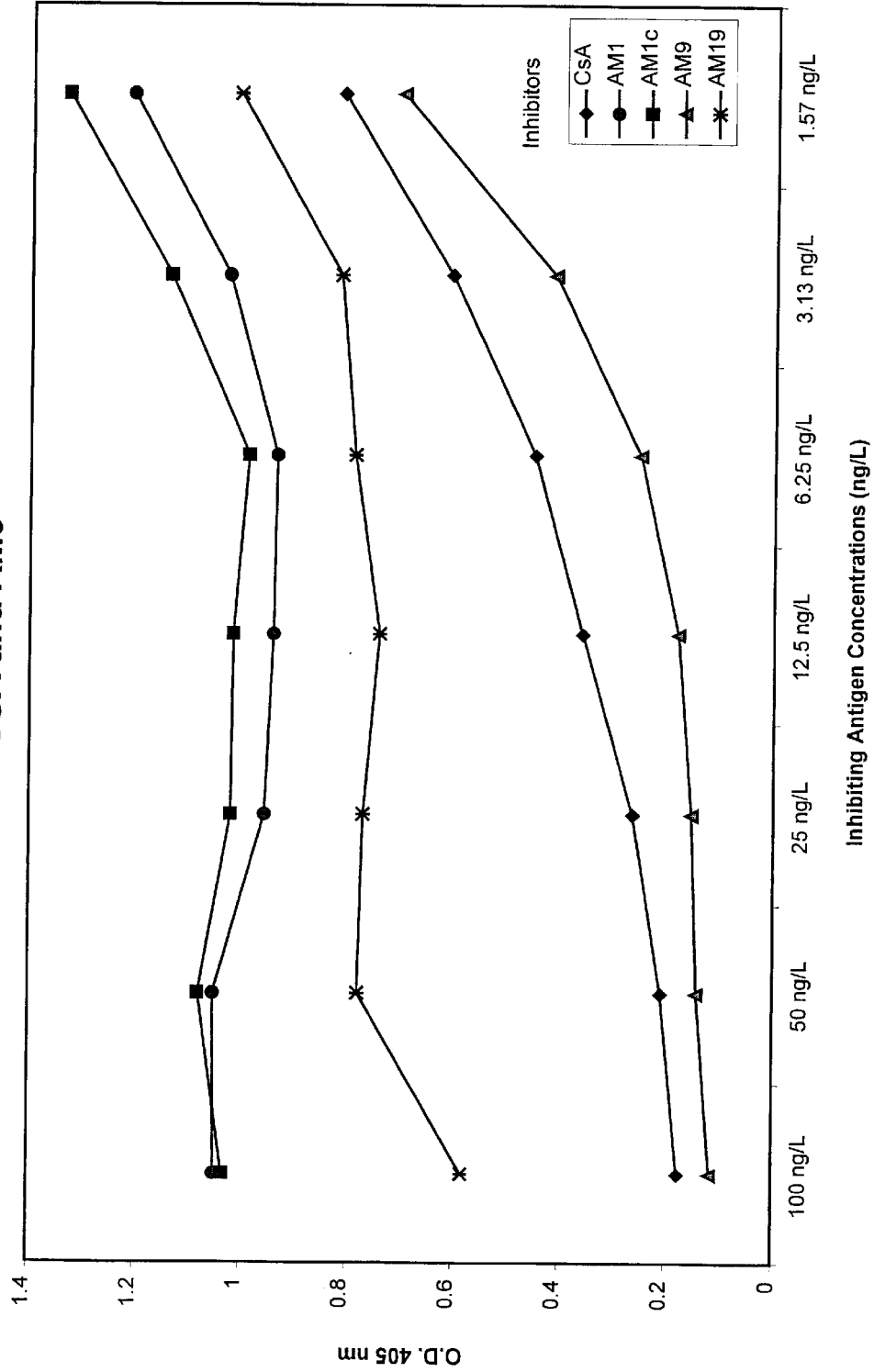
Figure 7: Inhibition ELISA of AM9-9-4F5 MoAb Showing Selectivity for CSA and AM9

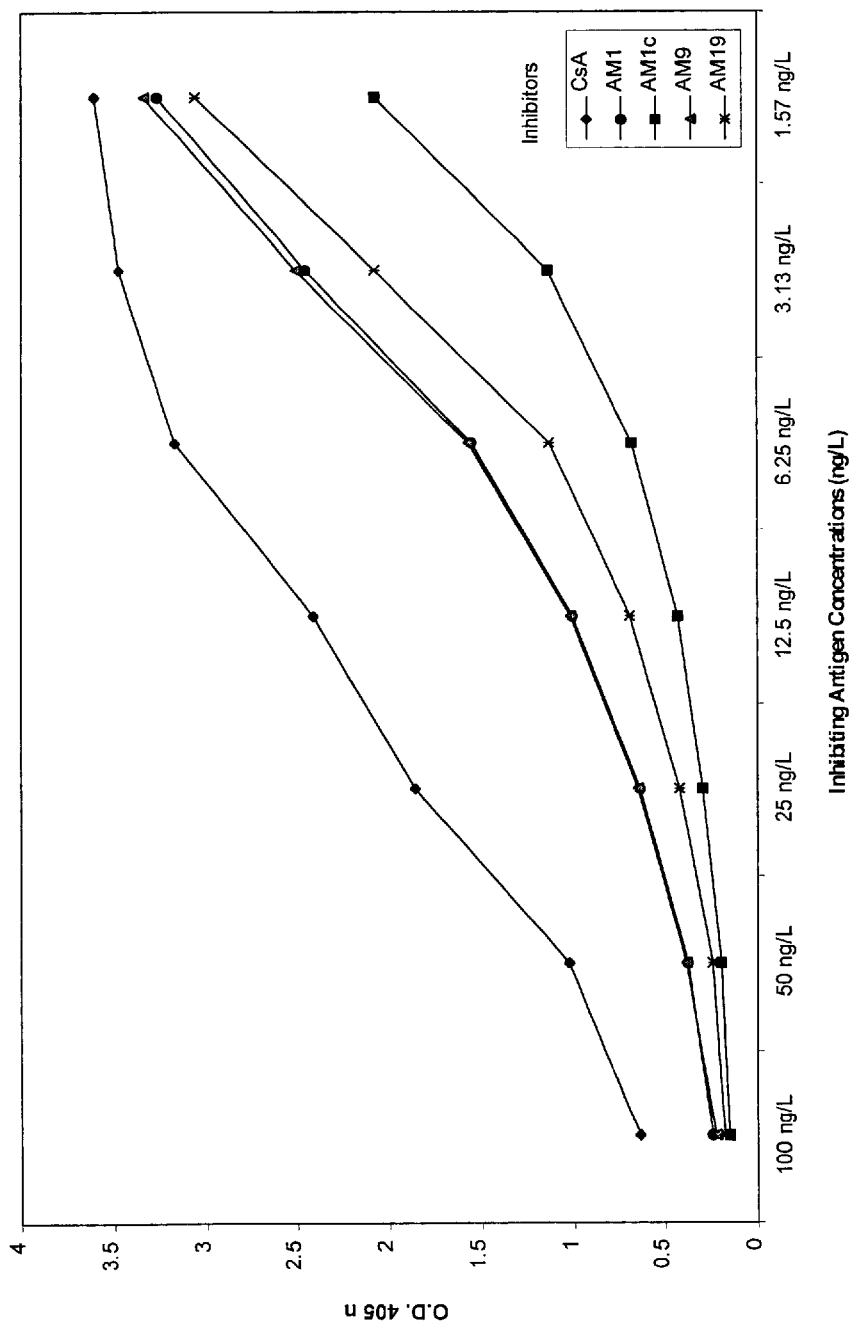

Figure 9: MLR Assay Procedure

Pop-A Lymphocytes (1x10$^5$cells/90 μl)          MoAbs (20 μg/20μl)
+                                                 or
Pop-B Lymphocytes (1x10$^5$cells/90 μl)          MoAbs (20 μg/10μL) + 10μL CsA(100μg/L)

Incubate MoAbs +/- CsA for 30 minutes R/T

Total volume 200 μl/well (round bottom 96-well microtiter plate)

DAY-0: Incubate at 37 C°, 5% $CO_2$, for 5-days

DAY-6: Pulse with [Methyl-$^3$H]- 20 μCi/ ml (30 μl/well)

Incubate at 37 C°, 5% $CO_2$, 18hours

DAY-7: Harvest into glass fiber membrane

Count (Gamma counter)

$$\% \text{ Proliferation} = \frac{\text{CPM (Test groups)}}{\text{CPM (Media Control)}} \times 100$$

% Inhibition= 100 - % Proliferation

ANTIBODIES TO SPECIFIC REGIONS OF CYCLOSPORINE RELATED COMPOUNDS

CROSS-REFERENCE TO RELATED APPLICATIONS

This application is a continuation-in-part of U.S. application Ser. No. 09/168,885 filed Oct. 9, 1998, now abandoned the entire disclosure of which is incorporated herein by reference.

FIELD OF THE INVENTION

This invention relates to the production of polyclonal and monoclonal antibodies to specific sites of cyclosporine and/or cyclosporine metabolites, derivatives and analogues. The reactivity of these polyclonal and monoclonal antibodies makes them particularly useful for immunoassays for therapeutic drug monitoring (TDM). These immunoassays or TDM kits may include polyclonal or monoclonal antibodies to specific sites of cyclosporine (CSA) and/or metabolites, derivatives and analogues of cyclosporine. These kits may also include various combinations of polyclonal antibodies, polyclonal and monoclonal antibodies or a panel of monoclonal antibodies.

BACKGROUND OF THE INVENTION

Cyclosporine is an 11-amino acid cyclic peptide of fungal origin (isolated from the fungus *Tolypocladium inflatum*) that contains two uncommon amino acids: (4R)-4-((E)-2butenyl)-4, N-dimethyl-1-threonine (Bmt) and I-alpha-aminobutyric acid (Abu), as well as several peptide bond N-methylated residues (residues 1, 3, 4, 6, 9, 10, and 11). The structure of cyclosporine is given in FIG. 1.

Currently, the two immunosuppressive drugs administered most often to prevent organ rejection in transplant patients are cyclosporine (CSA) and tacrolimus (FK-506 or FK). Rapamycin (Rapa) is another known immunnosuppressant. Cyclosporine's primary target appears to be the helper T lymphocytes. Cyclosporine acts early in the process of T cell activation, it has secondary effects on other cell types that are normally activated by factors produced by the T cells. Cyclosporine inhibits the production of interleukin 2 (IL-2) by helper T cells, thereby blocking T cell activation and proliferation (amplification of immune response). It is effective both in the prevention and in the treatment of ongoing acute rejection. The current model for the mechanism of action of CSA suggests that, in the T cell cytoplasm, CSA binds to a specific binding protein called immunophilin. The CSA-immunophilin complex in turn binds to and blocks a phosphatase called calcineurin. The latter is required for the translocation of an activation factor (NF-ATc) from the cytosol to the nucleus, where it would normally bind to and activate enhancers/promoters of certain genes. In the presence of CSA, the cytosolic activation factor is unable to reach the nucleus, and the transcription of IL-2 (and other early activation factors) is strongly inhibited. As a result of this inhibition, T cells do not proliferate, secretion of gamma-interferon is inhibited, no MHC class II antigens are induced, and no further activation of the macrophages occurs.

Various side effects are associated with cyclosporine therapy, including nephrotoxicity, hypertension, hyperkalemia, hypomagnesemia and hyperuricemia. Neuro- or nephrotoxicity has been correlated with certain cyclosporine metabolites. A necessary requirement of cyclosporine drug monitoring assays is to measure the levels of parent cyclosporine drug and metabolite with immunosuppressive and toxic activity. There is a need for improved methods of monitoring levels of CSA and/or CSA metabolites and derivatives.

SUMMARY OF THE INVENTION

The current invention is drawn to methods for the preparation of immunogenic conjugates which elicit antibodies with specificity for cyclosporine related compounds. For the purposes of this application, the term cyclosporine related compound is meant to include any or all of the cyclosporine molecule itself and/or various cyclosporine metabolites and derivatives. Cyclosporine and cyclosporine metabolite conjugate immunogens are prepared and used for the immunization of a host animal to produce antibodies directed against specific regions of the cyclosporine or metabolite molecules. By determining the specific binding region of a particular antibody, immunoassays which are capable of distinguishing between the parent molecule, active metabolites, inactive metabolites and other cyclosporine derivatives/analogues are developed. The use of divinyl sulfone (DVS) as the linker arm molecule for forming cyclosporine/metabolite-protein conjugate immunogen is described.

In a first aspect, the invention provides antibodies which are capable of binding to a cyclosporine related compound. Such antibodies which recognize a specific region of said cyclosporine related compound or the CSA metabolites AM1 or AM9 are preferred. Monoclonal antibodies are most preferred. Also provided are methods for producing, an antibody which is capable of recognizing a specific region of a cyclosporine related compound, said methods comprising: a) administering an immunogen comprising a cyclosporine related compound, a linker arm molecule and a protein carrier to an animal so as to effect a specific immunogenic response to the cyclosporine related compound; b) recovering an antibody to said cyclosporine related compound from said animal; and c) identifying the antibody binding region by comparing the reactivity of the antibody to a first cyclosporine related compound to the reactivity of the antibody to a second cyclosporine related compound. Such methods wherein said linker arm molecule is divinyl sulfone and where the cyclosporine related compound is linked to the carrier at amino acid residue 1 or 9 are preferred. The protein carrier may preferably be keyhole limpet hemocyanin or human serum albumin. Use of hybridoma cells to accomplish the above methods is also provided.

In another aspect, the invention provides immunoassay methods for measuring the level of a cyclosporine related compound in a mammal, comprising: a) incubating a biological sample from said mammal with an antibody which is capable of binding to a cyclosporine related compound; and b) measuring the binding of cyclosporine related compound to said antibody. Use of antibodies which recognize a specific region of said cyclosporine related compound or the CSA metabolites AM1 or AM9 in these assays is preferred. Use of monoclonal antibodies is most preferred: Immunoassay kits for measuring the level of a cyclosporine related compound in a biological sample, said kits comprising an antibody as described above are also provided. Also provided are assay methods for determining the amount of a particular cyclosporine related compound in a sample, comprising: a) contacting said sample with a first antibody according to claim 1; b) contacting said sample with a second antibody according to claim 1; and c) determining the amount of said particular cyclosporine related compound bound to said second antibody.

BRIEF DESCRIPTION OF THE DRAWINGS

FIG. 3 shows the selectivity of monoclonal antibody AM19-9-5A6 for the CSA metabolite AM1.

FIG. 4 illustrates a monoclonal antibody selective for the AM9 metabolite.

FIG. 5 shows the selectivity of monoclonal antibody AM19-1-7E 12 for the AM1 and AM1c moieties.

FIG. 6 illustrates an example of monoclonal antibodies (MoAbs) with selectivity for the AM1 and AM9 metabolites.

FIG. 7 shows the selectivity of MoAb AM9-9-4F5 for CSA and AM9.

FIG. 8 illustrates a MoAb with greater selectivity for AM1, AM1c, AM9 and AM19 metabolites than for the parent CSA molecule.

FIG. 9 illustrates an MLR assay procedure.

DETAILED DESCRIPTION OF THE INVENTION

The following examples describe the best mode for carrying out the invention. The examples describe isolation of CSA metabolites, preparation of haptens, immunization of animals to ellicit antibody responses, characterization of antibody reactivity, production and selection of polyclonal and monoclonal antibodies to CSA and CSA metabolites or derivatives and assays using the antibodies provided by the present invention.

The following Examples are not intended to limit the scope of the invention in any manner.

EXAMPLE 1

Isolation and Characterization of Cyclosporine Metabolites

Figure 1:
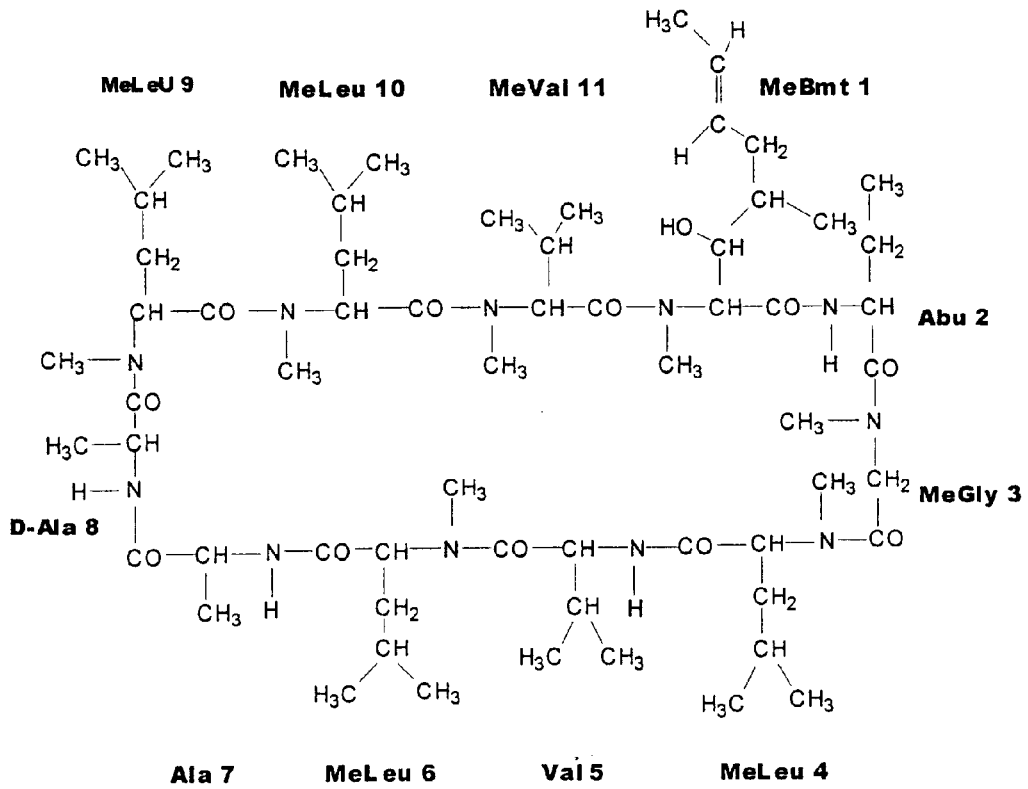
FIG. 1 [SEQ ID NO.:1] depicts the structure of cyclosporine A (CSA).
Figure 2:
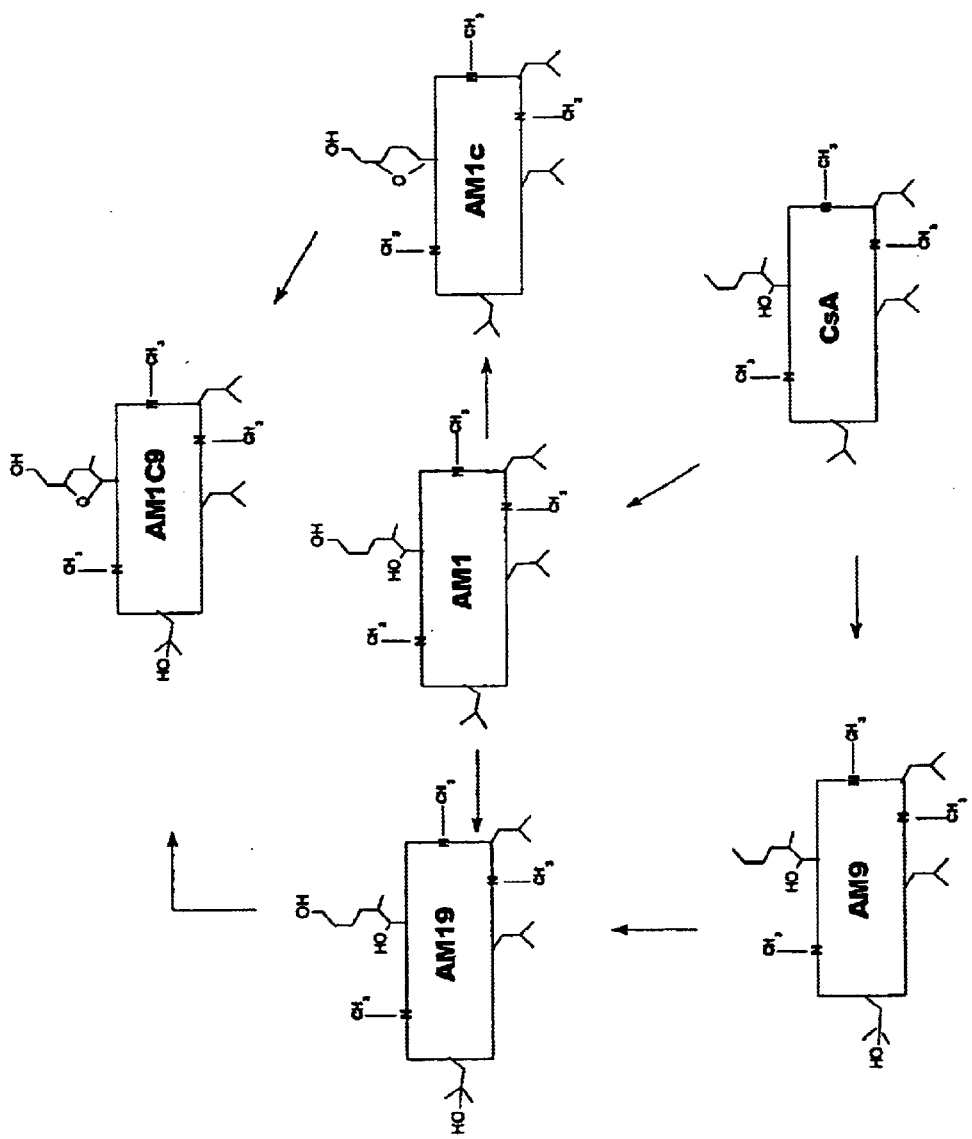
FIG. 2 [SEQ ID NO.:2–7] depicts the major metabolites of CSA and routes of its metabolism.

Cyclosporine is metabolized in the liver, small intestine and the kidney. The structures of various phase I and II metabolites have been identified by HPLC and mass spectrometry in the literature. The major metabolites of CSA are shown in FIG. 2. Metabolic reactions include oxidation and cyclisation at amino acid #1 and hydroxylation and demethylation at various amino acid sites.

10 minutes at a low speed. Pour contents into a separatory funnel; discard lower aqueous layer, evaporating the upper ether layer to dryness.

2. Metabolite Isolation:

Add 1.0 mL of HPLC grade methanol to dried down extract, vortex for 30 seconds and centrifuge at 2800 rpm for 2 minutes. Transfer the supernatant to an autosampler vial and inject urine using the following chromatographic conditions:

| Column | SPHERISORB ™ (silica-based spherical packing material manufactured by Phase Separations) S5 C8 | 10 × 250 mm |
|---|---|---|
| Guard column | SPHERISORB ™ (silica-based spherical packing material manufactured by Phase Separations) S5 C8 | 4.6 × 10 mm |

-continued

| Wavelength | 214 nm |
|---|---|
| Run time | 90 minutes |
| Column temperature | 60° C. |

W600 Gradient Table:

| Time (min) | Flow (mL) | H$_2$O % | ACN % | MeOH % |
|---|---|---|---|---|
| 0.00 | 4.00 | 41.0 | 39.0 | 20.0 |
| 55.00 | 4.00 | 41.0 | 39.0 | 20.0 |
| 55.01 | 4.00 | 30.0 | 50.0 | 20.0 |
| 65.00 | 4.00 | 30.0 | 50.0 | 20.0 |
| 65.01 | 4.50 | 5.0 | 0 | 95.0 |
| 85.00 | 4.50 | 5.0 | 0 | 95.0 |
| 85.01 | 4.50 | 41.0 | 39.0 | 20.0 |
| 89.80 | 4.50 | 41.0 | 39.0 | 20.0 |
| 89.90 | 4.00 | 41.0 | 39.0 | 20.0 |

Collect individual metabolites based on the following typical retention times:

| Retention time (min) | Modification | Metabolite species |
|---|---|---|
| 14.090 | hydroxylated on a.a. 1 and 9 | AM19 |
| 16.118 | hydroxylated on a.a. 1 and 9 cyclical on a.a. 1 side chain | AM1c9 |
| 22.065 | demethylated on a.a. 4 hydroxylated on a.a. 9 | AM4n9 |
| 32.252 | hydroxylated on a.a. 1 | AM1 |
| 33.852 | hydroxylated on a.a. 9 | AM9 |
| 35.929 | hydroxylated on a.a. 1 cyclical on a.a. 1 side chain | AM1c |
| 62.630 | demethylated on a.a. 4 | AM4n |
| 67.584 | NA | CSA |

The following are examples of the amounts of various metabolites recovered from 20L urine lots.

| | Lot P (from 20 L urine) | | Lot N (from 19 L urine) | | Lot O (from 20 L urine) | |
|---|---|---|---|---|---|---|
| Metabolite | Amount (µg) | % of Total | Amount (µg) | % of Total | Amount (µg) | % of Total |
| AM19 | 849 | 5.0 | 1053 | 7.7 | 719 | 3.9 |
| AM1c9 | 401 | 2.4 | 489 | 3.6 | 230 | 0.12 |
| AM4n9 | 1323 | 7.8 | 1071 | 7.8 | 786 | 4.2 |
| AM1 | 5640 | 33.2 | 4998 | 36.5 | 6600 | 35.5 |
| AM9 | 3624 | 21.3 | 2350 | 17.1 | 3852 | 20.7 |
| AM1c | 3814 | 22.5 | 2352 | 17.2 | 4766 | 25.6 |
| AM4n | 1332 | 7.8 | 1395 | 10.2 | 1643 | 8.8 |
| Totals | 16,983 | | 13,708 | | 18,596 | |

3. Quantitative Analysis of Metabolites:

Reconstitute isolated metabolite in 1 mL MeOH. Take 25 µL of this mixture and add 25 µL CSG (20,000 ng/mL) and 300 µL mobile phase, vortex and inject 100 µL to the HPLC under the following conditions:

| Column | SPHERISORB ™ (silica-based spherical packing material manufactured by Phase Separations) C8 | 4.6 × 250 mm |
|---|---|---|
| Temperature | 60° C. | |
| Flow | 1.0 mL/min | |
| Wavelength | 214 nm | |
| Mobile phase | 33% H$_2$O/47% ACN/20% MeOH | |

4. Metabolite Concentration:

(Peak area metabolite÷Peak area internal standard)×0.5 μg× (1/0.025)× dilution factor=μg of Metabolite Percent purity:

(conc. of metabolite peak μg/mL÷conc. of all peaks μg/mL)×100

5. Final Purification of CSA Metabolites:

The metabolites isolated in the first round of HPLC purification are not usually greater than 97% pure. Therefore, a second round of purification is required using a different HPLC column and mobile phase.

Inject reconstituted metabolites onto the HPLC using the following conditions:

| Column | Symmetry Prep C18 7 μm | 7.8 × 300 mm |
|---|---|---|
| Guard column | SPHERISORB ™ (silica-based spherical packing material manufactured by Phase Separations) S5 C8 | 4.6 × 10 mm |
| Wavelength | 214 nm | |
| Column temperature | 60° C. | |

A two solvent gradient, comprised of water and methanol, is utilized to purify the metabolites. The key to separation is the addition of methyl-tert-butyl-ether (MTBE) to the methanol portion of the mobile phase (use 70 mL MTBE per 500 mL methanol). The exact gradient utilized varies depending on the metabolite to be purified.

Example 2

Synthesis of CSA-Divinyl Sulfone and Conjugation to a Protein Carrier

1. Preparation of CSA-DVS Hapten:

Cyclosporine (30 mg, 25 mol, U.S. Pharmacopeia, Rockville, Md., Cat #15850-4 USP reference standard), vinyl sulfone (147 mg, 1.3 mmol) and benzyl triethylammonium chloride (11.4 mg, 50 μmol) were stirred in 6 mL dichloromethane and then 0.4 mL of 40% aqueous potassium hydroxide was added. The mixture was rapidly stirred for 1.5 hours, then acidified with 2M hydrochloric acid and diluted with dichloromethane. The organic phase was separated, washed with water, dried over magnesium sulfate and the solvent evaporated.

2. Analysis of CSA-DVS Hapten:

One (1) product with mass corresponding to CSA-DVS was identified by Liquid Chromatography-Electrospray Ionization Mass Spectrometry (LC/MS). The product was purified by HPLC (SPHERISORB™ (silica-based spherical packing material manufactured by Phase Separations) C-8 semi-prep column;80% methanol isocratic;4 mL/min;50° C.;214 nm). The result was 3.3 mg of pure CSA-DVS for which a 600 MHz proton nmr spectrum was obtained.

3. Preparation of CSA-DVS-protein Conjugates:

CSA-DVS (1.0 mg) was dissolved in 350 μL of dimethyl sulfoxide and slowly spiked into a rapidly stirred solution of keyhole limpet hemocyanin (KLH) (1.6 mg) in 1.2 mL of phosphate buffer (pH 7.6). The mixture was stirred at room temperature for 24 hours. This material was then dialyzed overnight against phosphate buffered saline (PBS). The concentration of protein was determined by the Lowry protein assay, the coupling of CSA to the protein was confirmed by gel electrophoresis and western blot analysis. Using human serum albumin (HSA), a CSA-DVS-HSA conjugate was prepared in the same manner. Other protein carriers known in the art may also be used to prepare CSA-DVS conjugates using these methods.

Example 3

Synthesis of AM1-Divinyl Sulfone and Conjugation to a Protein Carrier

1. Preparation of AM1-DVS Haptens:

AM1 (4.0 mg, 3.3 μmol), potassium carbonate (70 mg, 0.51 mmol) and a few crystals of 18-Crown-6 were dissolved in 4 mL of anhydrous acetone and the solution stirred at room temperature for 45 minutes. Vinyl sulfone (31.0 mg, 0.26 mmol) was then added and the reaction stirred overnight at room temperature. The mixture was then diluted with ethyl acetate and washed sequentially with water, dilute aqueous hydrochloric acid and brine (saturated ammonium chloride). The organic phase was then dried over magnesium sulfate and the solvent evaporated. Methanol was added to the residue and the methanol soluble portion was kept for purification. The reaction was repeated several times until sufficient product was obtained for purification and conjugation.

2. Analysis of AM1-DVS Haptens:

Two (2) main products with mass corresponding to AM1-DVS were identified by LC/MS. The products were purified by HPLC (SPHERISORB™ (silica-based spherical packing material manufactured by Phase Separations) C-8 semi-prep column; 80% methanol isocratic; 4 mL/min; 50° C.;214 nm). A 600 MHz proton nmr spectra has been obtained for both AM1-DVS (species 1) and AM1-DVS (species 2).

3. Preparation of AM1-DVS-protein Conjugates:

AM1 -DVS (species 1, 0.2 mg) was dissolved in 300 μL of dimethyl sulfoxide and slowly spiked into a rapidly stirred solution of KLH (1.0 mg) in 1.0 mL of phosphate buffer (pH 7.6). The mixture was stirred at room temperature for 24 hours and then dialyzed overnight against PBS. The concentration of protein was determined by the Lowry protein assay. AM1-DVS (species 2) was conjugated to KLH in the same manner. Human serum albumin (HSA) or other protein carriers known in the art may also be used as carriers to prepare AM1-DVS conjugates.

Example 4

Synthesis of AM19-Divinyl Sulfone and Conjugation to a Protein Carrier

1. Preparation of AM19-DVS Haptens:

AM19 (4.5 mg, 3.6 μmol), potassium carbonate (60 mg, 0.43 mmol) and a few crystals of 18-Crown-6 were mixed together in 5 mL of anhydrous acetone and the solution stirred at room temperature for 45 minutes. Vinyl sulfone (43.0 mg, 0.36 mmol) was then added and the reaction stirred overnight at room temperature. The solvent was evaporated by passing a stream of nitrogen gas through the reaction flask. The residue was immediately quenched with a mixture of 1N aqueous hydrochloric acid and ethyl acetate.

The organic phase was then diluted with ethyl acetate, washed sequentially with water and brine, and then dried over magnesium sulfate and the solvent evaporated. Methanol was added to the residue and the methanol soluble portion submitted for LC/MS purification. The reaction was repeated several times until sufficient product was obtained for purification and conjugation.

2. Analysis of AM19-DVS Haptens:

Three (3) products with mass corresponding to AM19-DVS (1375-Na adduct m/z) were identified by LC/MS. These products were assigned AM19-DVS (1), AM19-DVS (2) and AM19-DVS (3) for identification.

i) Identification, Purification and Characterization of AM19-DVS (1) Hapten:

AM19-DVS (1) was purified by HPLC (SPHERISORB™ (silica-based spherical packing material manufactured by Phase Separations) C-8 semi-prep column) as follows: Rotary evaporated AM19-DVS (1) from the crude collection was dissolved in 77% methanol, injected into the HPLC and run using the following conditions: 77% methanol isocratic; 4 mL/min; 35° C.; 214 nm. The collected material was rechromatographed until pure. The purity of AM19-DVS (1) was assessed from a mass spectrum and HPLC. The electrospray fragmentation profile of purified AM19-DVS (1) is consistent with DVS modification through the secondary hydroxyl of amino acid 1. For purposes of this application, this hapten will be referred to as AM19-1-DVS (1).

ii) Identification, Purification and Characterization of AM19-DVS (2) Hapten:

AM19-DVS (2) was purified by HPLC (SPHERISORB™ (silica-based spherical packing material manufactured by Phase Separations) C-8 semi-prep column) in two steps. Step 1: Rotary evaporated AM19-DVS (2) from the crude collection was dissolved in 80% methanol, injected into the HPLC and run using the following conditions: 80% methanol isocratic; 4 mL/min; 35° C.; 214 nm. Step 2: The collected material from Step 1 was freeze dried, dissolved in 64% methanol, injected into the HPLC and run using the following conditions: 64% methanol isocratic; 4 mL/min; 35° C.; 214 nm. The purity of the AM19-DVS (2) hapten was assessed from a mass spectrum and HPLC. The electrospray fragmentation profile of this purified AM19-DVS (2) hapten is consistent with DVS modification through the primary hydroxyl of amino acid 1. For purposes of this application, this hapten will be referred to as AM19-1-DVS (2).

iii) Identification, Purification and Characterization of AM19-DVS (3) Hapten: AM19-DVS (3) was purified by HPLC (SPHERISORB™ (silica-based spherical packing material manufactured by Phase Separations) C-8 semi-prep column) in two steps. Step 1: Rotary evaporated AM19-DVS (3) from the crude collection was dissolved in 60% methanol, injected into the HPLC and run using the following conditions: 76% methanol isocratic; 4 mL/min; 35° C.; 214 nm. The purity of the AM19-DVS (3) hapten was assessed from a mass spectrum and HPLC. The electrospray fragmentation profile of purified AM19-DVS (3) is consistent with DVS modification through the hydroxyl group of amino acid 9. For purposes of this application, this hapten will be referred to as AM19-9-DVS.

3. Preparation of AM19-DVS-protein Conjugates:

AM19-1-DVS (1), 0.4 mg, was dissolved in 250 μL dimethyl sulfoxide and slowly spiked into a rapidly stirred solution of KLH (1.0 mg) in 1.0 mL of phosphate buffer (pH 7.6). The mixture was stirred at room temperature for 24 hours and then dialyzed overnight against PBS. The concentration of protein was determined by the Lowry protein assay. AM19-1-DVS (2), 0.8 mg/KLH, 6.0 mg; AM19-9-DVS, 0.3 mg/KLH, 1.0 mg conjugates, and the corresponding HSA conjugates were prepared in the same manner. Other protein carriers known in the art may also be used as carriers to prepare AM19-DVS conjugates.

Example 5

Synthesis of AM9-Divinyl Sulfone and Coniugation to a Protein Carrier

1. Preparation of AM9-DVS Haptens:

AM9 (11.1 mg, 9.1 μmol), potassium carbonate (80 mg, 0.58 mmol) and a few crystals of 18-Crown-6 were mixed together in 5 mL of anhydrous acetone and the solution stirred at room temperature for 45 minutes. Vinyl sulfone (107.5 mg, 0.911 mmol) was then added and the reaction stirred overnight at room temperature. The solvent was evaporated by passing a stream of nitrogen gas through the reaction flask. The residue was immediately quenched with a mixture of 1N aqueous hydrochloric acid and ethyl acetate. The organic phase was then diluted with ethyl acetate, washed sequentially with water and brine, and then dried over magnesium sulfate and the solvent evaporated. Methanol was added to the residue and the methanol soluble portion submitted for LC/MS purification. The reaction was repeated several times until sufficient product was obtained for purification and conjugation.

2. Analysis of AM9-DVS Haptens:

Two (2) products with mass corresponding to AM9-DVS (1359-Na adduct m/z) were identified by LC/MS. These products were assigned as AM9-DVS (1) and AM9-DVS (2).

i) Identification, Purification and Characterization of AM9-DVS (1) Hapten:

AM9-DVS (1) was purified by HPLC (SPHERISORB™ (silica-based spherical packing material manufactured by Phase Separations) C-8 semi-prep column) as follows: Rotary evaporated AM9-DVS (1) from the crude collection was dissolved in 70% methanol, injected into the HPLC and run using the following conditions: 70% methanol isocratic; 4 mL/min; 35° C.; 214 nm. The purity of AM9-DVS (1) was assessed from a mass spectrum and HPLC. The electrospray fragmentation profile of purified AM9-DVS (1) is consistent with DVS modification through the hydroxyl group of amino acid 9. For purposes of this application, this hapten will be referred to as AM9-9-DVS.

ii) Identification, Purification and Characterization of AM9-DVS (2) Hapten:

AM9-DVS (2) was purified by HPLC (SPHERISORB™ (silica-based spherical packing material manufactured by Phase Separations) C-8 semi-prep column) as follows: rotary evaporated AM9-DVS (2) from the crude collection was dissolved in 70% methanol, injected into the HPLC and run using the following conditions: 70% methanol isocratic; 4 mL/min; 35° C.; 214 nm. The purity of AM9-DVS (2) was assessed from a mass spectrum and HPLC. The electrospray fragmentation profile of purified AM9-DVS (2) is consistent with DVS modification through the secondary hydroxyl group of amino acid 1. For purposes of this application, this hapten will be referred to as AM9-1-DVS.

3. Preparation of AM9-DVS-protein Conjugates:

AM9-9-DVS (0.4 mg) was dissolved in 300 μL of dimethyl sulfoxide and slowly spiked into a rapidly stirred solution of KLH (1.0 mg) in 1.0 mL of phosphate buffer (pH 7.6). The mixture was stirred at room temperature for 24 hours and then dialyzed overnight against PBS. The concentration of protein was determined by the Lowry protein assay. AM9-1-DVS-KLH and the corresponding HSA conjugates were prepared in a similar manner. Other protein carriers known in the art may also be used as carriers to prepare AM9-DVS conjugates.

Example 6

Immunization to Elicit CSA and/or CSA Metabolite/Derivative Specific Antibody Responses The basic immunization protocols are as follows: Typically, mice are immunized on day 0 (1°—primary immunization), day 7 (2°—secondary immunization), and day 28 (3°—tertiary immunization) by subcutaneous or intraperitoneal injection with CSA/CSA metabolite conjugate immunogens at doses of 5, 10, 15, or 20 μg based on protein content. Mice were bled 7–10 days post 2° and 3° immunization to collect serum to assay antibody responses. Various other immunization schedules are effective, including day 0 (1°), day 7 (2°) and days 14, 21 or 30 (3°); day 0 (1°), day 14 (2°), and days 28 or 44 (3°); and day 0 (1°), day 30 (2°) and day 60 (3°). Thirty days post-tertiary immunization a booster may be injected. Subsequent monthly boosters may be administered.

Immunized mice are I.V. or I.P. injected with immunogen in PBS as a final boost 3–5 days before the fusion procedure. This increases the sensitization and number of immunogen specific B-lymphocytes in the spleen (or lymph node tissues). This final boost is administered 2 to 3 weeks after the previous injection to allow circulating antibody levels to drop off.

Such immunization schedules are useful to immunize mice with CSA/CSA metabolite immunogen conjugates to elicit specific polyclonal antiserum and for the preparation of specific monoclonal antibodies. The immunogen compositions are also useful for immunizing any animal capable of eliciting specific antibodies to CSA and/or a CSA metabolite or derivative, such as bovine, ovine, caprine, equine, leporine, porcine, canine, feline and avian and simian species. Both domestic and wild animals may be immunized. The route of administration may be any convenient route, and may vary depending on the animal to be immunized, and other factors known to those of skill in the art. Parenteral administration, such as subcutaneous, intramuscular, intraperitoneal or intravenous administration, is preferred. Oral or nasal administration may also be used, including oral dosage forms, which are enteric coated.

Exact formulation of the compositions will depend on the species to be immunized and the route of administration. The immunogens of the invention can be injected in solutions such as 0.9% NaCl (w/v), PBS or tissue culture media or in various adjuvant formulations. Such adjuvants could include, but are not limited to, Freund's complete adjuvant, Freund's incomplete adjuvant, aluminum hydroxide, dimethyldioctadecylammonium bromide, Adjuvax (Alpha-Beta Technology), Imject Alum (Pierce), Monophosphoryl Lipid A (Ribi Immunochem Research), Titermax (CytRx), toxins, toxoids, glycoproteins, lipids, glycolipids, bacterial cell walls, subunits (bacterial or viral), carbohydrate moieties (mono-, di-, tri-, tetra-, oligo- and polysaccharide), dextran sulfate, various liposome formulations or saponins. Combinations of various adjuvants may be used with the immunogen conjugates of the invention to prepare a pharmaceutical composition.

The conjugates of this invention may be used as immunogens to elicit CSA and/or CSA metabolite/derivative specific polyclonal antibody, and to stimulate B-cells for specific monoclonal antibody production. They may also be utilized as development and/or research tools; as diagnostic reagents in immunoassay kit development; as prophylactic agents, for example, to block cell receptors; and as therapeutic modalities as immunomodulators and as drug delivery compositions.

Example 7

Assays to Determine Antibody Reactivity to CSA and/or CSA Metabolite Immunogens The basic direct ELISA protocol (Ag panel ELISA) for determining antibody reactivity to CSA or CSA metabolites used in the Examples was as follows:

Direct ELISA Protocol:
1. Use Falcon Pro-bind immunoplate.
2. Dilute coating antigen (Ag) to 1.0 g/mL in carbonate-bicarbonate buffer. Use glass tubes.
3. Add 100 μL to each well of plate. Store overnight at 4° C.
4. Shake out wells and wash 3× with 200 μL PBS/0.05% TWEEN™ (polyoxyethylene-sorbitol) (v/v) per well.
5. Add blocking buffer, 200 μL per well (PBS/2% BSA (w/v)). Incubate for 60 min at 37° C.
6. Wash 3× as in step 4.
7. Add 100 μL per well of test antibody appropriately diluted in PBS/0.1% Tween (v/v). Incubate 60 min at 37° C.
8. Wash 3× as in step 4.
9. Dilute alkaline phosphatase conjugated anti-mouse IgG (Pierce cat #31322) in PBS/0.1% Tween™ (polyoxyethylene-sorbitol) (v/v) to 1:2000 concentration. Add 100 μL per well and incubate at 37° C. for 60 min.
10. Wash 3× as in step 4.
11. Prepare enzyme substrate using Sigma #104 alkaline phosphatase substrate tablets (1 mg/mL in 10% diethanolamine (v/v) substrate buffer). Add 100 μL per well and incubate in the dark at room temperature. Absorbance can be read at 405 nm at approximately 15-min intervals.

To measure antibody isotype levels (IgM, IgG and IgA isotypes) elicited to CSA or CSA metabolite immunogens the following basic procedure was used:

Isotyping ELISA Protocol:
1. Use Falcon Pro-bind immunoplates.
2. Dilute coating antigen to 1 μg/mL in carbonate-bicarbonate buffer. Add 100 μL per well and incubate overnight at 4° C.
3. Shake out wells and wash 3× with 200 μL PBS/0.05% Tween™ (polyoxyethylene-sorbitol) (v/v) per well.
4. Add 200 μL blocking buffer per well (PBS/2% BSA (w/v)). Incubate 60 min at room temperature.
5. Wash as in step 3.
6. Add 100 μL per well of tissue culture supernatant undiluted or mouse serum diluted to 1/100 in PBS/0.1% Tween™ (polyoxyethylene-sorbitol) (v/v). Incubate for 60 min at 37° C.
7. Wash as in step 3.
8. Prepare 1:2 dilution of EIA grade mouse type (rabbit anti-mouse IgM, IgG1, IgG2a, IgG2b, IgG3 and IgA, Bio-Rad) in dilution buffer (PBS/0.1% TWEEN™ (polyoxyethylene-sorbitol) (v/v)). Add 100 μL per well into appropriate wells and incubate 60 min at 37° C.
9. Wash as in step 3.
10. Dilute alkaline phosphatase conjugated anti-rabbit IgG (Tago cat #4620) in PBS/0.1% TWEEN™ (polyoxyethylene-sorbitol) (v/v) to 1:2000 concentration. Add 100 μL per well and incubate at 37° C. for 60 min.

11. Wash as in step 3.
12. Prepare enzyme substrate using Sigma #104 alkaline phosphatase substrate tablets (1 mg/mL in 10% diethanolamine (v/v) substrate buffer). Add 100 μL per well and incubate in the dark at room temperature. Absorbance can be read at 405 nm at approximately 15-min intervals.
13. Absorbance readings may be converted to μg antibody per ml serum using dose-response curves generated from ELISA responses of the rabbit anti-mouse isotype antibodies to various concentrations of mouse class and subclass specific immunoglobulins (Zymed Labs. Inc.).

The following procedure was used to determine antibody binding to specific sites of CSA or CSA metabolites/derivatives and to quantify antibody cross-reactivity to FK-506, rapamycin, and KLH or HSA proteins.

Inhibition ELISA Protocol:
1. Use Falcon Pro-bind immunoplates.
2. Dilute coating antigen to 1 μg/mL in carbonate-bicarbonate buffer. Add 100 μL per well and incubate overnight at 4° C.
3. On the same day prepare inhibiting antigen tubes. Aliquot antibodies into glass test tubes. Prepare appropriate antigen concentration in ethanol and add to aliquoted antibody at 10 μL ethanol solution/250 μL antibody. Vortex tubes and incubate overnight at 4° C.
4. Shake out wells and wash 3× with 200 μL PBS/0.05% TWEEN™ (polyoxyethylene-sorbitol) (v/v) per well.
5. Add 200 μL blocking buffer per well (PBS/2% BSA (w/v)). Incubate 60 min at room temperature.
6. Wash as in step 4.
7. Transfer contents of inhibition tubes to antigen-coated plate, 100 μL per well. Incubate 60 min at 37° C.
8. Wash as in step 4.
9. Dilute alkaline phosphatase conjugated anti-mouse IgG (Pierce cat# 31322) in PBS/0.1 % TWEEN™ (polyoxyethylene-sorbitol) (v/v) to 1:5000 concentration. Add 100 μL per well and incubate at 37° C. for 60 min.
10. Wash as in step 4.
11. Prepare enzyme substrate using Sigma #104 alkaline phosphatase substrate tablets (1 mg/mL in 10% diethanolamine (v/v) substrate buffer). Add 100 μL per well and incubate in the dark at room temperature. Absorbance can be read at 405 nm at approximately 15-min intervals.

Buffers used in the direct, isotyping and inhibition ELISA protocols were:

| Coating buffer (sodium carbonate/bicarbonate 0.05 M. pH 9.6) | |
|---|---|
| Sodium carbonate (Fisher, cat # S-233-500) | 2.93 g |
| Sodium bicarbonate (Fisher, cat # S-263-500) | 1.59 g |
| adjust pH to 9.6 using 1 M HCl or 1 M NaOH | |
| store at 4° C. | |
| 10× PBS buffer | |
| Potassium phosphate, mono-basic (Fisher, cat P-284B-500) | 8.00 g |
| Sodium phosphate, di-basic (Fisher, cat # S-373-1) | 46.00 g |
| Sodium chloride (Fisher, cat # S-671-3) | 320.00 g |
| Potassium chloride (Fisher, cat # P-217-500) | 8.00 g |
| dissolve in 4 L distilled water | |
| store at room temperature | |
| Dilution buffer (1× PBS/0.1% TWEEN™ (polyoxyethylene-sorbitol)) | |
| 10× PBS | 50.0 mL |
| distilled water | 450 mL |
| TWEEN™ (polyoxyethylene-sorbitol)-20 | 0.5 mL |
| (Polyoxyethylene-sorbitol monolaurate | |
| Sigma, cat # P-1379) | |
| adjust pH to 7.2 and store at room temperature | |

| -continued | |
|---|---|
| Wash buffer (1× PBS/0.05% TWEEN™ (polyoxyethylene-sorbitol)) | |
| 10× PBS | 200 mL |
| distilled water | 1800 mL |
| Tween-20 | 1.0 mL |
| adjust pH to 7.2 and store at room temperature | |
| Blocking buffer (1× PBS/2% BSA) | |
| 1× PBS | 100 mL |
| Bovine Serum Albumin (Sigma, cat # A-7030) | 2.0 g |
| store at 4° C. | |
| Substrate buffer (10% diethanolamine) | |
| Diethanolamine (Fisher, cat # D-45-500) | 97.0 mL |
| Magnesium chloride (Fisher, cat # M-33-500) | 100.0 mg |
| adjust pH to 9.8 and store at 4° C. (protect from light) | |

The direct ELISA, isotyping and inhibition ELISA procedures have been described to detect mouse antibodies (poly- and monoclonal antibodies), however these procedures can be modified for other species, including but not limited to antibodies of rabbit, guinea pig, sheep or goat.

Example 8

Polyclonal Antibody Responses to the CSA-DVS-KLH Immunogen

Polyclonal antisera were prepared in mice using the CSA-DVS-KLH immunogen described in Example 2 and the immunization regimes described in Example 6. Individual mouse sera collected 10 days post-secondary and tertiary immunization were assayed for antibody titre by direct ELISA (as described in Example 7) and further screened by inhibition ELISA using CSA, CSA conjugate or KLH inhibitors. Examples of mouse polyclonal sera with good anti-CSA reactivity are shown in Table 1. CSA and CSA-DVS-HSA inhibited antibody binding to a CSA-DVS-HSA ELISA coated plate in a dose dependant manner. KLH or a FK-DVS-KLH conjugate did not inhibit antibody binding.

These mouse sera were further characterized by the antigen panel ELISA assay, results shown in Table 2. These results demonstrate that immunized mouse serum had good reactivity to the CSA-DVS, AM19-1-DVS (1), AM19-1-DVS (2) and AM9-1-DVS HSA conjugates. These sera had low reactivity to the AM19-9-DVS-HSA conjugate. This indicates that the antisera recognized epitopes on the CSA/CSA metabolite molecules and that DVS coupling through the 9 amino acid residue significantly reduced antibody reactivity (i.e., DVS linkage through the 9 amino acid residue blocks the epitope recognition site). These sera had specificity for the CSA antigen and did not react with the FK, Rapamycin or HSA antigens. A significant response to the KLH carrier molecule of the CSA-DVS-KLH conjugate was seen using KLH coated ELISA plates.

To further characterize this polyclonal antibody response, inhibition ELISA's to the CSA-DVS-HSA conjugate were performed. Results are shown in Table 3. The polyclonal sera were inhibited by CSA and all the CSA metabolites (some variability in binding to CSA metabolites was observed). These sera did not bind epitopes on the FK, Rapamycin, KLH or HSA molecules. These results show that the CSA-DVS-KLH immunogen elicits polyclonal antisera to CSA and CSA metabolites.

TABLE 1

Inhibition ELISA Showing CSA Specificity of Mouse Polyclonal Sera (CSA-DVS-KLH immunogen)

| Inhibiting Ag conc ($\mu$g/100 $\mu$L) | Mouse 1 | | | | Mouse 2 | | | |
|---|---|---|---|---|---|---|---|---|
| | CSA | CSA-DVS-HSA | KLH | FK-DVS-KLH | CSA | CSA-DVS-HSA | KLH | FK-DVS-KLH |
| 10 | 82.9 | 85.4 | 0 | 0 | 86.8 | 83.3 | 0 | 0 |
| 5 | 80.4 | 83.2 | 0 | 0 | 85.9 | 70.7 | 0 | 0 |
| 2.5 | 75.9 | 80.3 | 0 | 0 | 73.3 | 54.4 | 0 | 0 |
| 1.25 | 72.1 | 68.3 | 0 | 0 | 66.8 | 47.4 | 0 | 0 |
| 0.625 | 56.5 | 62.0 | 0 | 0 | 48.8 | 28.4 | 0 | 0 |
| 0.313 | 43.4 | 43.3 | 0 | 0 | 19.6 | 10.1 | 0 | 0 |
| 0.156 | 23.0 | 30.3 | 0 | 0 | 6.9 | 2.2 | 0 | 0 |

(results expressed as percent inhibition)

TABLE 2

Mouse Polyclonal Antibody Reactivity (CSA-DVS-KLH immunogen) to CSA, CSA Metabolite, FK, Rapamycin, KLH or HSA Antigens

| Antigen | Mouse 1 | | Mouse 2 | |
|---|---|---|---|---|
| Panel | OD | %* | OD | % |
| CSA-DVS-HSA | 0.991 | 100 | 0.977 | 100 |
| AM9-1-DVS-HSA | 1.304 | >100 | 1.218 | >100 |
| AM19-9-DVS-HSA | 0.290 | 29.3 | 0.453 | 46.4 |
| AM19-1-DVS-HSA (1) | 1.099 | >100 | 1.462 | >100 |
| AM19-1-DVS-HSA (2) | 1.212 | >100 | 1.128 | >100 |
| FK-DVS-HSA | 0.005 | 0 | 0.010 | 1.0 |
| Rapa-suc-HSA | 0 | 0 | 0 | 0 |
| HSA | 0 | 0 | 0 | 0 |

*Percent reactivity = OD to test antigen/OD to CSA-DVS-HSA × 100

TABLE 3

Percent Inhibition of Mouse Sera (CSA-DVS-KLH immunogen) with CSA/CSA Metabolites, Rapamycin, FK, KLH and HSA Antigens

| Inhibiting antigen | Mouse sera |
|---|---|
| CSA | 65.1 |
| AM1 | 96.2 |
| AM1c | 98.0 |
| AM4n | 59.5 |
| AM1c9 | 60.5 |
| AM19 | 57.2 |
| AM9 | 70.7 |
| FK | 31.9 |
| Rapamycin | 28.2 |
| KLH | 30.2 |
| HSA | 24.9 |

Example 9

Polyclonal Antibody Responses to the AM1-DVS-KLH Immunogen

Polyclonal antisera was prepared in mice using the AM1 immunogens described in Example 2 and the immunization regimes described in Example 6. Individual mouse sera collected 10 days post-secondary and tertiary immunizations were assayed for antibody titre by direct ELISA. Mice having high anti-CSA titres were assayed for specificity by antigen panel reactivity. Results are shown in Table 4.

These results show that mice immunized with the AM1-DVS antigen conjugated to KLH carrier displayed good antibody reactivity to the CSA antigen and cross-reactivity with the AM19-1-DVS (1), AM19-1-DVS (2) and AM9-1-DVS antigens. These sera had lower reactivity to the AM19-9-DVS antigen. As with the previous example, this indicates that the antisera recognized epitopes on the CSA/CSA metabolite conjugates when DVS coupling was through the 1 amino acid residue, but that DVS binding through the 9 amino acid residue significantly reduced antibody reactivity (i.e., masking antibody epitope recognition site). These sera were CSA/CSA metabolite epitope specific and did not react with the FK, Rapamycin or HSA antigens. These mice mounted a significant response to the KLH carrier of the immunogen conjugate.

To further characterize these polyclonal antibody responses, inhibition ELISA's to the CSA-DVS-HSA conjugate were performed as described in Example 7. Results are shown in Table 5. These polyclonal sera were inhibited by CSA and CSA metabolites. However, inhibition varied from 39–100%, depending on the inhibiting molecule. The polyclonal antisera were specific to CSA/CSA metabolites as no inhibition with FK, Rapamycin, HSA or KLH antigens was observed.

TABLE 4

Mouse Polyclonal Antibody Reactivity (AM1-DVS-KLH immunogens) to CSA, CSA Metabolite, FK, Rapamycin, KLH or HSA Antigens

| Antigen | Mouse 1 | | Mouse 2 | |
|---|---|---|---|---|
| Panel | OD | %* | OD | % |
| CSA-DVS-HSA | 0.780 | 100 | 0.622 | 100 |
| AM9-1-DVS-HSA | 1.037 | >100 | 0.966 | >100 |
| AM19-9-DVS-HSA | 0.483 | 61.9 | 0.583 | 93.7 |
| AM19-1-DVS-HSA (1) | 1.075 | >100 | 1.244 | >100 |
| AM19-1-DVS-HSA (2) | 0.982 | >100 | 1.187 | >100 |
| FK-DVS-HSA | 0 | 0 | 0 | 0 |
| Rapa-suc-HSA | 0 | 0 | 0 | 0 |
| HSA | 0 | 0 | 0 | 0 |

*Percent reactivity = OD to test antigen/OD to CSA-DVS-HSA × 100

TABLE 5

Percent Inhibition of Mouse Polyclonal Sera (AM1-DVS-KLH immunogen) with CSA/CSA Metabolites, Rapamycin, FK, KLH and HSA Antigens

| Inhibiting antigen | Mouse 1 | Mouse 2 |
|---|---|---|
| CSA | 96.6 | 56.2 |
| AM1 | 100 | 96.7 |
| AM1c | 96.9 | 99.5 |
| AM4n | 86.8 | 72.6 |
| AM1c9 | 75.6 | 92.7 |

TABLE 5-continued

Percent Inhibition of Mouse Polyclonal Sera (AM1-DVS-KLH immunogen) with CSA/CSA Metabolites, Rapamycin, FK, KLH and HSA Antigens

| Inhibiting antigen | Mouse 1 | Mouse 2 |
|---|---|---|
| AM19 | 39.2 | 84.7 |
| AM9 | 87.9 | 88.6 |
| FK | 3.5 | 13.0 |
| Rapamycin | 0 | 12.4 |
| KLH | 8.9 | 5.8 |
| HSA | 1.8 | 14.9 |

Example 10

Polyclonal Antibody Response to AM19-DVS-KLH Immunogens

Serum samples were collected 10 days post-secondary and tertiary immunization (as described in Example 6) with AM19-1-DVS (1), AM19-1-DVS (2) or AM19-9-DVS KLH conjugates (as described in Example 4). These serum samples were assayed by direct ELISA for antibody titre to specific haptens. Sera showing high antibody reactivity to AM19 were further characterized by antigen panel ELISA (Table 6).

Sera from mice 1 and 2 (AM19-1-DVS (1) hapten) had good reactivity to CSA/CSA metabolite epitopes and did not cross-react to Rapamycin, FK or HSA epitopes. Sera from Mice 3 and 4 (AM19-1-DVS (2) hapten) also reacted to CSA/CSA metabolite epitopes. Modification of amino acid #9 (DVS coupled to amino acid 9) decreased antibody binding. These sera did not cross-react with epitopes on the Rapamycin, FK or HSA molecules. All mice displayed significant antibody titres to the KLH carrier protein.

Inhibition ELISA results (Table 7), demonstrate variable polyclonal antibody reactivity to the CSA metabolites and little or no inhibition with the CSA parent molecule.

TABLE 6

Mouse Polyclonal Antibody Reactivity (AM19-1-DVS-KLH immunogens) to CSA, CSA Metabolite, FK, Rapamycin, KLH or HSA Antigens

| Antigen Panel | Mouse 1* OD | %*** | Mouse 2* OD | % | Mouse 3** OD | % | Mouse 4** OD | % |
|---|---|---|---|---|---|---|---|---|
| CSA-DVS-HSA | 2.135 | 65.1 | 2.741 | 90.5 | 0.994 | 70.4 | 1.534 | 59.6 |
| AM9-1-DVS-HSA | 2.683 | 81.8 | 2.920 | 96.4 | 1.372 | 97.2 | 2.134 | 82.9 |
| AM19-9-DVS-HSA | 3.17 | 96.6 | 2.409 | 79.6 | 0.646 | 45.8 | 1.091 | 42.4 |
| AM19-1-DVS-HSA(1) | 3.281 | 100 | 3.028 | 100 | 1.181 | 83.7 | 2.351 | 91.4 |
| AM19-1-DVS-HSA(2) | 3.020 | 92.0 | 3.188 | >100 | 1.411 | 100 | 2.573 | 100 |
| FK-DVS-HSA | 0 | 0 | 0 | 0 | 0 | 0 | 0 | 0 |
| Rapa-suc-HSA | 0 | 0 | 0.036 | 1.2 | 0 | 0 | 0 | 0 |
| HAS | 0 | 0 | 0 | 0 | 0 | 0 | 0 | 0 |

*AM19-1-DVS (1)-KLH immunogen
**AM19-1-DVS (2)-KLH immunogen
***Percent reactivity = OD to test antigen/OD to AM19-1-DVS (1) or (2) × 100

TABLE 7

Percent Inhibition of Mouse Polyclonal Sera (AM19-1-DVS-KLH immunogen) with CSA/CSA Metabolites

| Inhibiting antigen | Mouse 1* | Mouse 2* | Mouse 3** | Mouse 4** |
|---|---|---|---|---|
| CSA | 4.9 | 23.4 | 0.2 | 4.7 |
| AM1 | 35.3 | 53.6 | 58.3 | 64.7 |
| AM1c | 76.6 | 87.2 | 76.8 | 82.7 |
| AM4n | 26.3 | 50.1 | 44.1 | 47.3 |
| AM1c9 | 75.0 | 88.2 | 61.5 | 69.0 |
| AM19 | 68.5 | 85.6 | 42.3 | 60.8 |
| AM9 | 57.9 | 75.9 | 46.1 | 50.3 |
| FK | 0 | 0 | 0 | 0 |
| Rapamycin | 0 | 0 | 0 | 0 |
| KLH | 0 | 0 | 0 | 0 |
| HAS | 0 | 0 | 0 | 0 |

*AM19-1-DVS (1) HSA coated plate
**AM19-1-DVS (2) HSA coated plate

The AM19-1-DVS (1) conjugate was also used to immunize rabbits. Reactivity of the polyclonal sera is shown in the inhibition ELISA results of Table 8 (AM19-1-DVS (1) HSA coated plate). As seen with the mouse serum, this rabbit sera did not recognize the CSA molecule and showed variable reactivity to the CSA metabolites and strongly bound to AM1c, AM1c9, AM19 and AM9 metabolites. There was no cross-reactivity to Rapamycin, FK, KLH or HSA antigens.

TABLE 8

Percent Inhibition of Rabbit Polyclonal Sera (AM19-1-DVS-KLH (1) immunogen) with CSA/CSA Metabolites

| Inhibiting antigen | Rabbit sera |
|---|---|
| CSA | 0 |
| AM1 | 55.2 |
| AM1c | 89.5 |
| AM4n | 55.2 |
| AM1c9 | 97.2 |
| AM19 | 97.2 |
| AM9 | 94.7 |
| FK | 0 |
| Rapamycin | 0 |
| KLH | 0 |
| HAS | 0 |

Sera from mice immunized with the AM19-9-DVS immunogen showing high reactivity to the AM19-9-DVS hapten were further characterized by antigen panel ELISA (Table 9). Significant antibody titres to the KLH carrier was observed.

Sera from mice 5 and 6 (AM19-9-DVS hapten) recognized epitopes on AM19-9-DVS hapten. Modification of the amino acid#1 (CSA-DVS, AM9-1-DVS or AM19-1 (2)) inhibited antibody binding. It is assumed that the antibody recognition site is on or near the amino acid 1 face of the molecule.

Polyclonal sera, when tested by inhibition ELISA using AM19-9-DVS-HSA coated plates, showed different results. Sera from mouse 5 demonstrate recognition of CSA and CSA metabolite epitopes. As this is a polyclonal serum the immunogen may elicit antibodies to epitopes of the parent CSA molecule as well as modified epitopes of the metabolites. With mouse 6, it appears the immunogen elicited only antibodies to the modified epitopes of the metabolites, no antibody to CSA epitopes was produced. With both sera there was no cross-reactivity to Rapamycin, FK, KLH or HSA antigens. Results are presented in Table 10.

TABLE 9

Mouse Polyclonal Antibody Reactivity (AM19-9-DVS-KLH immunogens) to CSA, CSA Metabolite, FK, Rapamycin, KLH or HSA Antigens

| Antigen Panel | Mouse 5 OD | %* | Mouse 6 OD | % |
|---|---|---|---|---|
| CSA-DVS-HSA | 0.002 | 0 | 0.017 | 0 |
| AM9-1-DVS-HSA | 0.232 | 7.2 | 0.457 | 14.0 |
| AM19-9-DVS-HSA | 3.231 | 100 | 3.267 | 100 |
| AM19-1-DVS-HSA (1) | 3.411 | >100 | 3.022 | 92.5 |
| AM19-1-DVS-HSA (2) | 0.167 | 5.2 | 0.968 | 29.6 |
| FK-DVS-HSA | 0.033 | 1.0 | 0.032 | 0 |
| Rapa-suc-HSA | 0.020 | 0 | 0.033 | 0 |
| Has | 0.012 | 0 | 0.007 | 0 |

*Percent reactivity = OD to test antigen/OD to AM19-9-DVS-HSA × 100

TABLE 10

Percent Inhibition of Mouse Polyclonal Sera (AM19-9-DVS-KLH immunogen) with CSA/CSA Metabolites

| Inhibiting antigen | Mouse 5 | Mouse 6 |
|---|---|---|
| CSA | 87.9 | 19.9 |
| AM1 | 96.2 | 67.6 |
| AM1c | 92.5 | 58.7 |
| AM4n | 77.9 | 36.3 |
| AM1c9 | 91.0 | 30.2 |
| AM19 | 97.8 | 55.4 |
| AM9 | 95.1 | 52.5 |
| FK | 0 | 0 |
| Rapamycin | 0 | 0 |
| KLH | 0 | 0 |
| HAS | 0 | 0 |

Example 11

Polyclonal Antibody Response to AM9-DVS-KLH Immunogens

Polyclonal antisera was prepared in mice using the AM9-1-DVS or AM9-9-DVS conjugates described in Example 5 and the immunization regimes as described in Example 6. Individual serum samples were collected 10 days post-secondary and tertiary immunization and assayed by direct ELISA for antibody titre to the corresponding hapten. Titres to the KLH carrier molecule were also quantified by direct ELISA.

Sera from mice immunized with the AM9-1-DVS conjugate which showed high antibody (Ab) reactivity to the specific hapten were then further characterized by antigen panel ELISA (Table 11). Sera from these mice recognized the CSA hapten, the AM9-1, AM19-1 (1) and (2) hapten conjugates (i.e., the AM9-1-DVS hapten would present the modified (hydroxylated) a.a. #9 face of the molecule for immune recognition). No reactivity to Rapamycin, FK, KLH or HSA epitopes was observed. The reduction in antibody binding to the AM19-9 hapten is presumed to be due to masking of the epitope recognition site, (i.e., blocking the modified a.a. #9 residue with the DVS linker arm would thereby block Ab/Ag interaction). The results of the inhibition ELISA (Table 12, AM9-1-DVS-HSA coated plate) demonstrate that the polyclonal antisera do not strongly recognize epitopes on the CSA, parent molecule, and show variable reactivity for the CSA metabolites. The AM9-1 DVS immunogen may be used to prepare and isolate MoAbs to various CSA metabolites. Screening for specific anti-AM9 MoAbs can also be achieved.

TABLE 11

Mouse Polyclonal Antibody Reactivity (AM9-1-DVS-KLH immunogen) to CSA, CSA Metabolites, FK, Rapamycin, KLH or HSA Antigens

| Antigen Panel | Mouse 1 OD | %* | Mouse 2 OD | % |
|---|---|---|---|---|
| CSA-DVS-HAS | 1.486 | 76.6 | 1.702 | 69.7 |
| AM9-1-DVS-HAS | 1.941 | 100 | 2.443 | 100 |
| AM19-9-DVS-HAS | 1.119 | 57.7 | 1.644 | 67.3 |
| AM19-1-DVS-HSA (1) | 2.683 | >100 | 2.750 | >100 |
| AM19-1-DVS-HSA (2) | 2.171 | >100 | 2.859 | >100 |
| FK-DVS-HAS | 0 | 0 | 0 | 0 |
| Rapa-suc-HAS | 0 | 0 | 0 | 0 |
| HAS | 0 | 0 | 0 | 0 |

*Percent reactivity = OD to test antigen/OD to AM9-1-DVS-HSA × 100

TABLE 12

Percent Inhibition of Mouse Polyclonal Sera (AM9-1-DVS-KLH immunogen) with CSA/CSA Metabolites

| Inhibiting antigen | Mouse 1 | Mouse 2 |
|---|---|---|
| CSA | 3.2 | 17.8 |
| AM1 | 61.5 | 41.6 |
| AM1c | 94.3 | 75.4 |
| AM4n | 25.1 | 43.8 |
| AM1c9 | 70.7 | 80.8 |
| AM19 | 57.9 | 74.2 |
| AM9 | 47.7 | 74.6 |

Sera from mice immunized with the AM9-9-DVS immunogen which reacted strongly to the AM19-9-DVS hapten were further characterized by antigen panel ELISA (Table 13). Sera from these mice recognize epitopes on the AM19-9-DVS-HSA molecule. However, DVS coupling through amino acid #1 appears to abrogate or significantly reduce antibody binding, as seen with the CSA, AM9-1, AM19-1 (1) and AM19-1 (2)-HSA conjugates. The reduction in antibody binding to panel antigens coupled through the a.a.#1 residue is presumed to be due to masking of the Ab epitope recognition site. As the AM9-9-DVS immunogens would present the a.a. #1 face of the molecule for immune recognition, blocking the a.a. #1 residue with the DVS linker arm would thereby block Ab/Ag interaction. Mouse sera did not cross-react with Rapamycin, FK or HSA antigens, significant antibody titres to the KLH carrier protein was observed.

The results of the inhibition ELISA (Table 14, AM19-9-DVS-HSA coated plate) demonstrate that these polyclonal sera recognize epitope sites on the CSA parent molecule and the CSA metabolites. The AM9-9-DVS hapten may be used to prepare and isolate MoAbs to CSA parent and various CSA metabolites.

TABLE 13

Mouse Polyclonal Antibody Reactivity (AM9-9-DVS-KLH immunogen) to CSA, CSA Metabolites, FK, Rapamycin, KLH or HSA Antigens

| Antigen Panel | Mouse 1 OD | %* | Mouse 2 OD | % | Mouse 3 OD | % |
|---|---|---|---|---|---|---|
| CSA-DVS-HSA | 0.032 | 1.0 | 0 | 0 | 0 | 0 |
| AM9-1-DVS-HSA | 0.252 | 8.2 | 0 | 0 | 0 | 0 |

TABLE 13-continued

Mouse Polyclonal Antibody Reactivity (AM9-9-DVS-KLH immunogen) to CSA, CSA Metabolites, FK, Rapamycin, KLH or HSA Antigens

| Antigen Panel | Mouse 1 OD | %* | Mouse 2 OD | % | Mouse 3 OD | % |
|---|---|---|---|---|---|---|
| AM19-9-DVS-HSA | 3.077 | 100 | 0.618 | 100 | 1.802 | 100 |
| AM19-1-DVS-HSA (1) | 0.018 | 0 | 0 | 0 | 0.777 | 43.1 |
| AM19-1-DVS-HSA (2) | 0.015 | 0 | 0 | 0 | 0 | 0 |
| FK-DVS-HSA | 0.016 | 0 | 0 | 0 | 0.046 | 2.6 |
| Rapa-suc-HSA | 0.048 | 1.6 | 0 | 20.2 | 0 | 0 |
| HSA | 0.001 | 0 | 0.060 | 9.7 | 0 | 0 |

*Percent reactivity = OD to test antigen/OD to AM19-9-DVS-HSA × 100

TABLE 14

Percent Inhibition of Mouse Polyclonal Sera (AM9-9-DVS-KLH immunogen) with CSA/CSA Metabolites

| Inhibiting antigen | Mouse 1 | Mouse 2 |
|---|---|---|
| CSA | 65.4 | 83.9 |
| AM1 | 66.2 | 83.9 |
| AM1c | 71.9 | 78.9 |
| AM4n | 51.9 | 57.7 |
| AM1c9 | 60.8 | 65.9 |
| AM19 | 32.7 | 69.0 |
| AM9 | 82.3 | 88.1 |
| FK | 24.2 | 34.5 |
| Rapamycin | 16.9 | 24.1 |
| KLH | 12.3 | 35.8 |
| HSA | 24.6 | 26.8 |

Example 12

A Method for Monoclonal Antibody Production (MoAb)

The steps for monoclonal antibody production are summarized below:

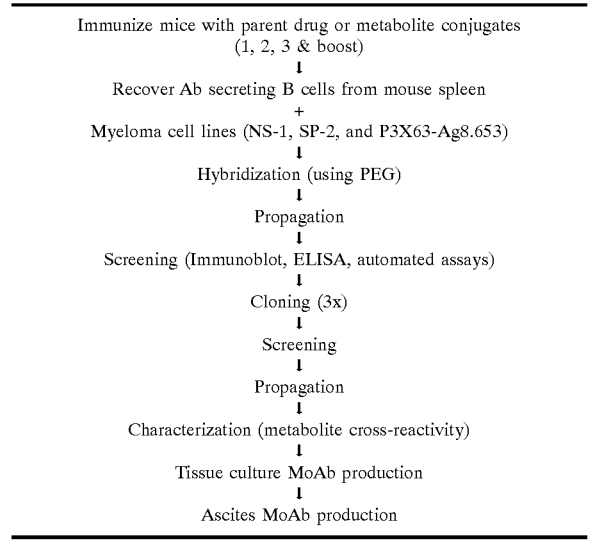

Although there are many suitable reagent suppliers, we have found the following to be most preferred for obtaining a high yield of fusion products, for isolating stable clones and for the production of monoclonal antibodies.

Dulbecco's Modified Eagles Medium: (DMEM) from JRH BIOSCIENCES, Cat #56499-10L+3.7 g/L NaHCO3.

HAT supplement: (100×—10 mM sodium hypoxanthine, 40 mM aminopterin, 1.6 mM thymidine) from CANADIAN LIFE TECHNOLOGIES, Cat #31062-037.

HT stock: (100×—10 mM sodium hypozanthine, 1.0 mM thymidine) from CANADIAN LIFE TECHNOLOGIES, Cat #11067-030.

FCS: CPSR-3 Hybrid-MAX from SIGMA, Cat#C-9155.

Polyethylene glycol (PEG): Use PEG 4000, SERVA #33136. Autoclave PEG, cool slightly and dilute to 50% w/v with serum free DMEM. Make fresh PEG the day before the fusion, and place in 37° incubator.

Fusion Procedure:

Myeloma cells should be thawed and expanded one week before fusion and split the day before the fusion. Do not keep the myeloma cell line in continuous culture. This prevents the cells from becoming infected with mycoplasma and also from any changes, which may result from repeated passaging.

For example:

SP2/0 can be split back to $1×10^4$ cells/mL, freeze at least $5×10^6$ cells/vial NS-1 can be split back to $1×10^4$ cells/mL, freeze at least $5×10^6$ cells/vial P3X63-Ag8.653 can be split back to $1×10^4$ cells/ml, freeze at least $5×10^6$ cell/vial Culture the myeloma cell line so that you will have at least $0.5×10^7$ cells (in log phase growth) on the day of the fusion. Three to five days prior to fusion, boost the immunized mouse. The mouse must be genotypically compatible with the myeloma cell line. Myeloma cell drug sensitivity should be confirmed.

Serum should be tested for its ability to support growth of the parental myeloma cell line. To test batches of serum, clone the parental myeloma cells (as outlined under cloning) in 10%, 5%, 2.5%, and 1% FCS. No feeder layer is required. Check growth and cell viability daily for 5 days.

Fusion Day

1. Place fresh medium, FCS to be used in fusion in water bath.
2. Harvest myeloma cells and wash 3× with serum-free medium (DMEM, RPMI or other commercially available tissue culture media may be used).
3. Remove spleen (lymph node cells may also be used) from immunized mouse; resterilize instruments or use new sterile instruments between each step, i.e., cutting skin, cutting abdominal muscle, removing spleen.
4. Rinse outside of spleen 3× by transferring to plastic petri plates containing sterile medium; use sterile forceps between each step.
5. Place spleen in plastic petri dish with serum-free medium in it, cut into 4 pieces and push gently through screen with sterile glass plunger to obtain a single cell suspension.
6. Centrifuge spleen cells in 50-mL conical centrifuge tubes at 300×g (1200 rpm in silencer) for 10 minutes.
7. Resuspend in 10 ml medium. Dilute an aliquot 100× and count cells.
8. Centrifuge rest of spleen cells, resuspend and recentrifuge. Myeloma cells can be washed at the same time. The NS-1, SP2/0 and P3X63Ag8 myeloma cell lines are most preferred, however other myeloma cell lines known in the art may be utilized. These include, but are not limited to, the mouse cell lines: X63Ag8.653, FO, NSO/1, FOX-NY; rat cell lines; Y3-Ag1.2.3, YB2/0 and IR983F and various rabbit and human cell lines.
9. Add myeloma and spleen cells together in 5:1 or 10:1 ratio with spleen cells in excess.

10. Recentrifuge: spleen cells and myeloma have now been washed 3×.
11. Gently flick pellet and place in incubator for 15 minutes to reach 37° C.

Fusion Protocol:

1. Add 1 mL of 50% PEG (w/v) solution over 1 minute stirring (add 0.25 mL ¹⁄₁₅ sec) holding tube in 37° C. water bath (beaker with warm water). PEG fuses membranes of myeloma with antibody secreting (B) cells.
2. Stir 1 minute holding in 37° C. water bath. Solution will turn lumpy.
3. Add 1 mL medium at 37° C. over 1 minute stirring.
4. Add another mL medium over 1 minute stirring.
5. Add 8 mL medium over 2 minutes stirring.
6. Centrifuge for 10 minutes at 300×g (1200 rpm in silencer) and pipet off supernatant.
7. Add 10 mL medium +20% FCS (v/v) to cells in tube and pour into plastic petri dish.
8. Leave in incubator with 5% $CO_2$ at 37° C. for 1–3 hours. This enhances stability of fusion products.
9. Plate cells out at a concentration of $2 \times 10^5$ cells per well in medium (100 µL/well).
10. Feed cells 100 µL of 2×HAT in medium the next day. No feeder layer is necessary at this time Feed fusion products 100 µL medium+HAT selection additive on day 3.

Hybridoma cells (myeloma:spleen cell hybrids) are selected by the addition of the drug aminopterin which blocks the de novo synthesis pathway of nucleotides. Myeloma:spleen hybrid cells can survive by use of the salvage pathway. Unfused myeloma cells and myeloma:myeloma fusion products have a defect in an enzyme of the salvage pathway and will die. Unfused spleen cells from the immunized mouse do not grow in tissue culture. Other drugs known in the art may be used to select myeloma:spleen cell hybrids, such as methotrexate or azaserine.

Feed fusion products 100 µL medium+HAT+spleen/thymus feeder layer if necessary on day 5 ($1 \times 10^5$ cells/well). Fibroblasts, RBC's or other cell types may also be used as feeder layers.

Continue to feed cells medium+HAT for 1 week, by day 7 post-fusion, change to medium+HT. Clones should appear 10–14 days after fusion.

Note:
1. Washing of the spleen cells, myeloma cells and steps 1–6 of the fusion protocol are performed with serum-free medium.
2. Thymocytes die in about 3 days, non-fused spleen cells in about 6 days.
3. Hybrids are fairly large and almost always round and iridescent.
4. T-cell and granulocyte colonies may also grow. They are smaller cells.

To Clone Hybrid Cells:

1. Resuspend the 200 µL in the well with a sterile eppendorf pipet tip and transfer to a small 5-mL sterile tube.
2. Add 200 µL medium (20% FCS v/v) to the original well. This is a safety precaution of the cloning procedure. Parent cells may also be transferred to 24 well plates as a precaution.
3. Take 20 µL of the hybrid cell suspension from step 1 and add 20 µL of eosin or trypan blue solution. Under 40× magnification hybrid cells appear to be approximately the same size and morphology as the myeloma cell line.
4. Clone viable cells by limiting dilution with:
    20% FCS (v/v) used in fusion medium
    1×HT
    $1 \times 10^6$ thymocytes per ml
    clone 1400 cells per cloning protocol Dilution Cloning Procedure:

Make 10 mL of thymocyte cloning suspension in DMEM with 20% FCS (v/v). Take 1400 hybrid cells and dilute to 2.8 mL.

Row 1: Plate 8 wells (200 µL/well)→100 cells/well.
    To the remaining 1.2 mL add 1.2 mL medium.
Row 2: Plate 8 wells (200 µL/well)→50 cells/well.
    To the remainder add 2.0 mL medium.
Row 3: Plate 8 wells (200 µL/well)→10 cells/well
    To the remainder add 1.2-mL medium.
Row 4: Plate 8 wells (200 µL/well)→5 cells/well.
    To the remainder add 2.8 mL medium.
Rows 5 & 6: Plate 16 wells (200 µL/well)→1 cell/well.

After cloning and screening for positive wells, re-clone the faster growing, stronger reacting clones. To ensure that a hybridoma is stable and single-cell cloned, this cloning is repeated 3 times until every well tested is positive. Cells can then be grown up and the tissue culture supernatants collected for the monoclonal antibody. Other limiting dilution cloning procedures known in the art, single-cell cloning procedures to pick single cells, and single-cell cloning by growth in soft agar may also be employed.

Monoclonal Antibody Production:

Monoclonal antibodies can be readily recovered from tissue culture supernatants. Hybrid cells can be grown in tissue culture media with FCS supplements or in serum-free media known in the art. Large-scale amounts of monoclonal antibodies can be produced using hollow fibre or bioreactor technology. The concentration, affinity and avidity of specific monoclonal antibodies can be increased when produced as ascitic fluid.

Ascitic Fluid Production:

1. Condition mice by injecting (I.P.) 0.5 mL pristane (2, 6, 10, 14-tetramethylpentadecane) at least 5 days before hybrid cell are injected. Mice should be genotypically compatible with cells injected, i.e., Balb/c mice should be used with NS-1 or SP2/0 fusion products. Mice of non-compatible genotype may be used if irradiated before cells are injected. However, Balb/c pristane treated mice are the best to use.
2. Inject (I.P.) $10^6$ (or more) hybrid cells in PBS. Wash cells 3× prior to injection to remove the FCS.
3. Mice will be ready to tap in about 7–14 days. Use an 18½ G needle to harvest ascites cells and fluid.
4. Transfer at least $10^6$ ascites cells from these mice to more pristane treated mice.
5. Ascites cells can be frozen in 10% DMSO (v/v), 20% FCS (v/v), DMEM medium. Freeze about $5 \times 10^6$ cells per vial. Monoclonal antibodies prepared in tissue culture or by ascitic fluid may be purified using methods known in the art.

Example 13

Isolation and Characterization of Monoclonal Antibodies to Specific Sites of CSA and/or CSA Metabolites/Derivatives The steps to isolate and characterize monoclonal antibodies with reactivity to a specific site(s) of CSA or CSA metabolites are outlined below:

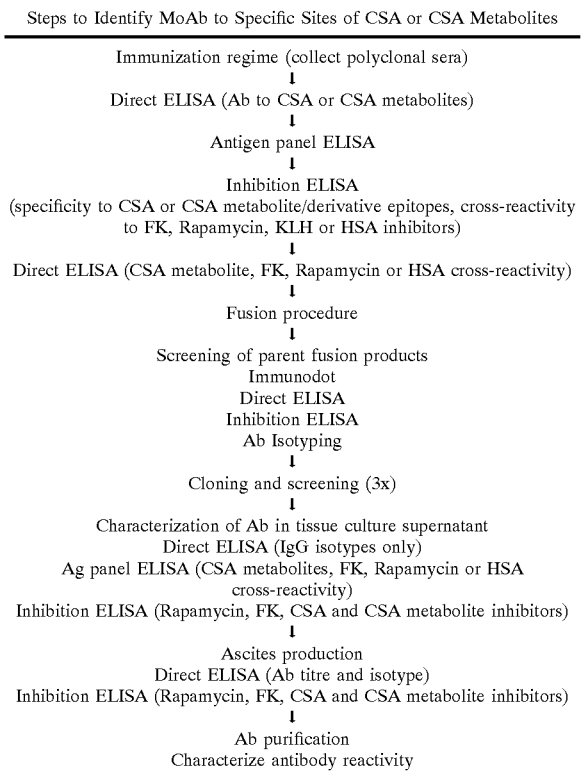

Immunodot Assay
1. Dot 5–10 µL of antibody onto nitrocellulose paper, which has been gridded for reference.
2. Air-dry and immerse nitrocellulose in PBS/0.1% TWEEN™ (polyoxyethylene-sorbitol) (v/v)/5% Milk (w/v) to block non-specific binding sites. Incubate at room temperature for 60 min with shaking.
3. Rinse twice with PBS/0.05% TWEEN™ (polyoxyethylene-sorbitol) (v/v) and wash with shaking for 10 min.
4. Dilute alkaline phosphatase conjugated anti-mouse IgG (Tago cat #AMI4405) in PBS/0.1% TWEEN™ (polyoxyethylene-sorbitol)(v/v) to 1:2000. Place nitrocellulose on parafilm or saran wrap and add diluted conjugated antibody until nitrocellulose is covered. Incubate covered at 37° C. for 60 min. Do not allow nitrocellulose to dry out between steps.
5. Wash as in step 3.
6. Prepare enzyme substrate using BCIP/NBT (Canadian Life Technologies, cat #18280-016; 88 µL NBT and 66 µL BCIP in 20 mL substrate buffer, 100 mM Tris, 5 mM $MgCl_2$, 100 mM NaCl). Place nitrocellulose in substrate solution and shake at room temperature for 10–30 min, watching for color development.
7. Rinse nitrocellulose with water to stop reaction.

Once antibody secreting parent fusion products were identified, the tissue culture supernatants were further characterized for CSA/CSA metabolite reactivity by the direct, isotyping and inhibition ELISA assays as described in Example 7. Tissue culture supernatants from clones (3×) of CSA/CSA metabolite positive parent fusion products were then characterized by isotyping ELISA to isolate IgG producing clones, by direct ELISA to determine antibody titre, by Ag panel ELISA to determine CSA/CSA metabolite reactivity and to determine FK and HSA cross-reactivity, and by inhibition ELISA using Rapamycin, CSA, FK and CSA metabolites to further demonstrate specificity and determine CSA site reactivity.

Using the immunodot and direct ELISA assays many parent fusion products were identified which have strong reactivity to the CSA and metabolite antigens. We have now isolated many IgM and IgG secreting clones with reactivity to the CSA and metabolite antigens by direct, Ag panel, inhibition and isotyping ELISA assays.

Example 14

Monoclonal Antibodies Elicited to the CSA-DVS Immunogen

Spleen cells from mice immunized with the CSA-DVS conjugate have been used to prepare monoclonal antibody secreting hybridoma clones. IgM and IgG anti-CSA secreting clones have been isolated. Table 15 illustrates the reactivity of tissue culture supernatants (TCS) from two of these anti-CSA MoAbs (CSA-1H6 and CSA-2G9).

These two MoAbs show good reactivity (high OD's) to CSA-DVS, AM9-1-DVS, AM19-1-DVS (1) and AM19-1-DVS (2) panel antigens (i.e., haptens coupled through the #1 amino acid residue). Reduction in MoAb binding to the AM19-9-DVS hapten indicates that DVS coupling through the #9 amino acid residue reduces Ab/epitope binding (i.e., this area of the CSA molecule is important or part of the epitope recognition site). CSA-1H6 and CSA-2G9 were specific to CSA epitopes and did not cross-react to epitopes on the FK, Rapamycin, KLH or HSA molecules.

To further characterize the specificity of CSA-1H6 and CSA-2G9 MoAbs, inhibition ELISA assays to the CSA-DVS-HSA conjugate were performed. Table 16 shows that TCS from CSA-1H6 and CSA-2G9 are inhibited by the parent CSA molecule (CSA-2G9 more strongly inhibited) and the AM1 and AM1c metabolites. Inhibition with the AM4n, AM1c9, AM19 and AM9 metabolites is significant. TCS from CSA-1H6 and CSA-2G9 MoAb clones are specific to CSA/CSA metabolite epitopes and do not cross-react with Rapamycin, FK, KLH and HSA. CSA-1H6 and CSA-2G9 can be used in a TDM assay to measure CSA parent molecule and CSA metabolite levels.

Table 15

Mouse Monoclonal Antibody (CSA-1H6, CSA-2G9) Reactivity to CSA, CSA Metabolites, FK, Rapamycin, KLH or HSA Antigens

| Antigen Panel | CSA-1H6 | | CSA-2G9 | |
|---|---|---|---|---|
| | OD | %* | OD | % |
| CSA-DVS-HSA | 1.515 | 100 | 2.752 | 100 |
| AM9-1-DVS-HSA | 1.904 | >100 | 2.978 | >100 |
| AM19-9-DVS-HSA | 0.511 | 33.7 | 0.323 | 11.7 |
| AM19-1-DVS-HSA (1) | 1.390 | 91.7 | 2.731 | >100 |
| AM19-1-DVS-HSA (2) | 1.870 | >100 | 3.219 | >100 |
| FK-DVS-HSA | 0 | 0 | 0.029 | 1.1 |
| Rapa-suc-HSA | 0 | 0 | 0.006 | 0 |
| HSA | 0.006 | 0 | 0 | 0 |
| KLH | 0 | 0 | 0.026 | 0 |

(CSA-1H6 and CSA-2G9 are both IgG1 antibody isotypes)
*Percent reactivity = OD to test antigen/OD to CSA-DVS-HSA × 100

TABLE 16

Percent Inhibition of TCS from CSA-1H6 and CSA-2G9 MoAb Clones with CSA/CSA Metabolites, Rapamycin, FK, KLH and HSA Antigens

| Inhibiting Antigen | CSA-1H6 | CSA-2G9 |
|---|---|---|
| CSA | 62.5 | 92.6 |
| AM1 | 98.0 | 98.2 |
| AM1c | 99.1 | 98.8 |
| AM4n | 98.8 | 64.3 |
| AM1c9 | 72.7 | 79.4 |
| AM19 | 62.4 | 76.4 |
| AM9 | 78.3 | 71.4 |
| Rapamycin | 0 | 10.4 |
| FK | 0 | 10.8 |
| HSA | 0 | 1.5 |
| KLH | 0 | 4.8 |

Example 15

Monoclonal Antibodies Elicited to the AM1-DVS Immunogens

Spleen cells from mice immunized with the AM1-DVS conjugates have been used to prepare monoclonal antibody secreting hybridoma cells. IgM and IgG anti-CSA MoAbs have been isolated by direct ELISA to CSA-DVS-HSA conjugates. Table 17 illustrates the reactivity of TCS from two of these monoclonal antibody clones (AM1-2E10 and AM1-7F5).

As with the monoclonal antibodies elicited by the CSA-DVS hapten, the MoAbs elicited to the AM1-DVS haptens have good affinity for CSA-DVS, AM9-1-DVS, AM19-1-DVS (1) and AM19-1-DVS (2) panel antigens (i.e., haptens coupled with the DVS linker through the #1 amino acid residue). Similarly, reduction in MoAb binding to the AM19-9-DVS hapten demonstrates that DVS coupling through the #9 amino acid residue decreases Ab/epitope binding. These results indicate that AM1-2E10 and AM1-7F5 are specific to CSA and CSA metabolite epitopes, they do not recognize epitopes on FK, Rapamycin, KLH or HSA molecules.

The specificity of TCS from AM1-2E10 and AM1-7F5 MoAb clones was further characterized by inhibition ELISA to the CSA-DVS-HSA conjugate. Table 18 demonstrates that AM1-2E10 is inhibited by the parent CSA molecule and all CSA metabolites. This MoAb does not cross-react with any epitope on Rapamycin, FK, KLH or HSA molecules. AM1-2E10 can be utilized in a TDM assay to measure CSA parent molecule and all CSA metabolite levels.

With AM1-7F5, the AM1 and AM1c metabolites strongly inhibit MoAb binding to the CSA-DVS-HSA coated plate. Less but significant inhibition was found with the CSA parent molecule and AM4n, AM1c9, AM19 and AM9 metabolites. Rapamycin, FK, KLH and HSA showed no significant inhibition. This result demonstrates that AM1-7F5 can be used in a TDM assay to measure CSA and CSA metabolite levels. Under certain TDM assay conditions (i.e., MoAb dilution), AM1-7F5 may also be used to selectively measure the levels of AM1 and AM1c metabolites.

TABLE 17

Mouse Monoclonal Antibody Reactivity (AM1-DVS-KLH immunogen) to CSA, CSA Metabolites, FK, Rapamycin, KLH or HSA Antigens

| Antigen | AM1-2E10 | | AM1-7F5 | |
|---|---|---|---|---|
| Panel | OD | %* | OD | % |
| CSA-DVS-HSA | 1.546 | 100 | 1.971 | 100 |
| AM9-1-DVS-HSA | 1.750 | >100 | 2.465 | >100 |
| AM19-9-DVS-HSA | 0.270 | 17.5 | 0.790 | 40.1 |
| AM19-1-DVS-HSA (1) | 1.546 | 100 | 2.283 | >100 |
| AM19-1-DVS-HSA (2) | 1.793 | >100 | 3.372 | >100 |
| FK-DVS-HSA | 0.015 | 0 | 0 | 0 |
| Rapa-suc-HSA | 0.015 | 0 | 0.008 | 0 |
| KLH | 0.061 | 3.9 | 0 | 0 |
| HSA | 0.006 | 0 | 0 | 0 |

(AM1-2E10 is an IgG2b and AM1-7F5 is an IgG1 antibody isotype)
*Percent reactivity = OD to test antigen/OD to CSA-DVS-HSA × 100

TABLE 18

Percent Inhibition of TCS from AM1-2E10 and AM1-7F5 MoAb Clones with CSA/CSA Metabolites, Rapamycin, FK, KLH and HSA Antigens

| Antigen | AM1-2E10 | AM1-7F5 |
|---|---|---|
| CSA | 81.9 | 53.8 |
| AM1 | 100 | 99.5 |
| AM1c | 100 | 100 |
| AM4n | 85.7 | 57.5 |
| AM1c9 | 100 | 56.2 |
| AM19 | 100 | 60.0 |
| AM9 | 100 | 62.3 |
| Rapamycin | 0 | 25.4 |
| FK | 0 | 26.0 |
| KLH | 0 | 22.5 |
| HSA | 0 | 16.1 |

Example 16

Monoclonal Antibodies Elicited to the AM19-DVS Immunopens

Spleen cells from mice immunized with the AM19-1-DVS (1) conjugate have been used to prepare MoAb secreting hybridoma cells. Anti-AM19-1-DVS (1) ELISA reactive IgM and IgG MoAb isotypes have been isolated. Table 19 illustrates the reactivity of TCS from two of these anti-AM19-1-DVS MoAbs (AM19-1-7E12-1 and AM19-1-7E12-2).

These two MoAb TCSs have high reactivity to the CSA-DVS, AM9-1-DVS, AM19-9-DVS, AM19-1-DVS (1) and AM19-1-DVS (2) panel antigens. These monoclonals did not cross react to Rapamycin, FK, KLH or HSA antigens. Using the more specific inhibition ELISA with AM19-1-DVS (1) coated ELISA plates, the CSA parent molecule did not inhibit antibody binding, the AM1c metabolite strongly inhibited binding of these MoAbs, AM1 and AM1c9 significantly inhibited MoAb binding, AM4n, AM19 and AM9 moderately inhibited binding, and Rapamycin, FK, KLH and HSA showed no inhibition of MoAb binding (Table 20).

Under specific TDM assay conditions (i.e., MoAb dilution) the level of AM1c metabolite may be quantified; the assay parameters may also be modified to selectively identify all CSA metabolite levels while not reacting to the CSA parent molecule.

TABLE 19

Mouse Monoclonal Antibody Reactivity (AM19-DVS-KLH immunogen) to CSA, CSA Metabolites, FK, Rapamycin, KLH or HAS Antigens

| Antigen | AM19-1-7E12-1 | | AM19-1-7E12-2 | |
|---|---|---|---|---|
| Panel | OD | %* | OD | % |
| CSA-DVS-HSA | 3.229 | 100 | 3.477 | >100 |
| AM9-1-DVS-HSA | 3.268 | >100 | 3.167 | 95.5 |
| AM19-9-DVS-HSA | 2.883 | 89.4 | 2.132 | 64.3 |
| AM19-1-DVS-HSA (1) | 3.226 | 100 | 3.316 | 100 |
| AM19-1-DVS-HSA (2) | 3.405 | >100 | 3.504 | >100 |
| FK-DVS-HSA | 0.029 | 0 | 0 | 0 |
| Rapa-suc-HSA | 0 | 0 | 0 | 0 |
| HAS | 0.009 | 0 | 0 | 0 |
| KLH | 0.023 | 0 | 0 | 0 |

(AM19-1-7E12-1 and AM19-1-7E12-2 are both IgG1 antibody isotypes)
*Percent reactivity = OD to test antigen/OD to AM19-1-DVS (1)-HSA × 100

TABLE 20

Percent Inhibition of TCS from AM19-1-7E12-1 and AM19-1-7E12-2 MoAb Clones with CSA/CSA Metabolites, Rapamycin, FK, KLH and HSA Antigens

| Antigen | AM19-1-7E12-1 | AM19-1-7E12-2 |
|---|---|---|
| CSA | 0 | 0 |
| AM1 | 59.2 | 67.3 |
| AM1c | 99.6 | 99.8 |
| AM4n | 30.4 | 36.8 |
| AM1c9 | 64.6 | 71.6 |
| AM19 | 35.2 | 49.5 |
| AM9 | 43.0 | 44.3 |
| Rapamycin | 7.7 | 8.6 |
| FK | 6.3 | 3.2 |
| KLH | 3.8 | 4.3 |
| HSA | 3.5 | 1.5 |

Similarly, MoAbs were prepared using the AM19-1-DVS (2) and AM19-9-DVS hapten-protein conjugate immunogens. For example, the AM19-1-DVS (2) and AM19-9-DVS conjugates were used to develop specific MoAbs to AM1 or AM9 metabolites. The ability of the AM19-1 and AM19-9 immunogens are not limited to MoAb development of AM1or AM9 metabolite residues; they may also be used to prepare MoAbs to other CSA metabolite residues and epitopes on the parent CSA molecule. Examples of MoAb's reactivity elicited to AM19-9 haptens is shown in Table 21.

TABLE 21

Percent Inhibition of TCS from AM19-9-1E11, AM19-9-5A6 and AM19-9-2G9 MoAb Clones with CSA/CSA Metabolites

| Antigen | AM19-9-1E11 | AM19-9-5A6 | AM19-9-2G9 |
|---|---|---|---|
| CSA | 96 | 72 | 28 |
| AM1 | 99 | 95 | 80 |
| AM1c | 99 | 68 | 20 |
| AM4n | 93 | 58 | 25 |
| AM1c9 | 96 | 61 | 47 |
| AM19 | 99 | 74 | 82 |
| AM9 | 99 | 44 | 85 |

*These TCS had no cross-reactivity to Rapamycin, FK, KLH or HSA.

Example 17

Monoclonal Antibodies Elicited to the AM9-DVS Immunogens

Using the methods disclosed in this application, spleen cells from mice immunized to the AM9-DVS-KLH conjugates can be used to prepare monoclonal antibody secreting hybridoma cells. The AM9-1-DVS-KLH and AM9-9-DVS-KLH immunogens can be used to elicit MoAbs with specificity for the AM1, AM1c and AM9 metabolite moieties. MoAbs to other CSA/CSA metabolite antigens may also be prepared using these immunogens (Table 22)

TABLE 22

Percent Inhibition of TCS from AM9-1-9H5, AM9-1-2A11, AM9-9-4F5 and AM9-9-6C3

| Antigen | AM9-1-9H5 | AM9-1-2A11 | AM9-9-4F5 | AM9-9-6C3 |
|---|---|---|---|---|
| CSA | 6 | 18 | 36 | 57 |
| AM1 | 45 | 53 | 25 | 58 |
| AM1c | 94 | 82 | 13 | 52 |
| AM4n | 21 | 15 | 22 | 50 |
| AM1c9 | 41 | 28 | 6 | 40 |
| AM19 | 24 | 19 | 6 | 37 |
| AM9 | 21 | 40 | 99 | 99 |

*These TCS had no cross-reactivity to Rapamycin, FK, KLH or HSA.

Example 18

Selectivity of Purified Monoclonal Antibodies

To confirm the reactivity and selectivity of MoAbs of this invention, purified MoAb was prepared from tissue culture supernatants. To purify MoAbs the following procedure was used:

Antibody Purification Protocol:

Thaw a frozen vial of monoclonal cells and grow to 200 ml in DMEM+Supplements (10% CPSR-3, 1%Penicillin/Streptomycin, 1% L-Glutamine, 1% Sodium pyruvate) until confluent. Incubate at 37° C., 5% $CO_2$ incubator.

1. Harvest concentrated supernatant by centrifuging at 1200 RPM, 10 minutes, 4° C. Balance pH of concentrated supernatant to pH 7.
2. Prepare Protein G column according to instructions (GammaBind Plus Spharose, Code No. 17-0886-02, Pharmacia Biotech).
3. Load concentrated supernatant on Protein G column at R/T.
4. Wash column with 25 ml of Binding buffers (0.01 M sodium phosphate, 0.15 M NaCl, 0.01 EDTA, pH 7.0).
5. Elute column with 15–20 ml of Elution buffer (0.5 M acetic acid pH 3.0).
6. Collect fractions using fraction collector (ISCO, FOXY Jr.).
7. Neutralize the eluted fractions with 0.5 ml of Neutralizing buffer (1 M Tris-HCl, pH 9.0)
8. Measure optical density of eluted fractions at 280 ηm wavelength (BECKMAN SpectrophotometerDU640i).
9. Pool fractions together in Spectra/Por membrane MWCO: 6-8000 (SPECTRUM, #132653)
10. Dialyze against 1×PBS at 4° C., O/N.
11. Do protein assay using BSA as standards (0, 200, 400, 600, 800, 1000 mg/ml). Read O.D. at 280 ηm wavelength.

Other antibody purification methods known in the art can be used. Using the competitive inhibition ELISA, MoAb cross-reactivity to a panel of hydroxylated or demethylated CSA metabolites was determined. The MoAbs to metabolite hapten conjugates of this invention can be separated into at least six groups based on their selectivity. Selectivity of various MoAbs purified from tissue culture supernatant is shown in Table 23.

TABLE 23

Purified MoAb Selectivity

| Clone Reference | | Purified MoAb Selectivity* |
| --- | --- | --- |
| Gp I: | AM1-2E10 | AM1 |
| | AM19-9-5A6 | AM1 (FIG. 3) |
| | AM9-1-6D4 | AM1 |
| Gp II: | AM9-1-7D2 | AM9 (FIG. 4) |
| | AM9-9-11G9 | AM9 |
| | AM9-9-6C3 | AM9 |
| Gp III: | AM1-3A6 | AM1, AM1c |
| | AM19-1-7E12 | AM1, AM1c (FIG. 5) |
| | AM9-1-2A11 | AM1, AM1c |
| Gp IV: | AM19-9-1E11 | AM1, AM9 |
| | AM19-9-1D8 | AM1, AM9 |
| | AM19-9-2G9 | AM1, AM9 (FIG. 6) |
| Gp V: | AM9-9-11H11 | CSA, AM1, AM9 |
| | AM9-9-4F5 | CSA, AM9 (FIG. 7) |
| Gp VI: | AM9-1-4D6 | AM1, AM1c, AM9, AM19 (FIG. 8) |

*This selectivity was determined by inhibition ELISA format.

MoAbs in group I are selective for the AM1 metabolite, FIG. 3 shows the selectivity of MoAb AM19-9-5A6 for the AM1 metabolized residue.

Example 19

Monoclonal Antibodies to CSA Derivatives

The specificity of the CSA-1H6, CSA-2G9, AM1-2E10, AM1-7F5 and AM19-7E12-1 MoAbs were also analyzed using CSA, CSA derivative and CSG inhibitors (Table 24).

As demonstrated previously, these MoAbs were inhibited by the parent CSA molecule. Deuteration of the amino acid #1 residue of the CSA molecule did not affect Ab epitope site recognition. Their binding to the ELISA plate was inhibited by this CSA derivative. MoAbs CSA-1H6 and CSA-2G9 have good affinity for the cyclosporine G (CSG) molecule. The AM1 MoAbs show moderate (AM1-2E10=61% inhibition) to low (AM1-7F5=28.8% inhibition) affinity for CSG.

This data demonstrates that CSA-1H6, CSA-2G9, AM1-2E10 and AM1-7F5 have good affinity for the CSA molecule and a CSA derivative modified on the amino acid #1 residue. CSA-1H6 and CSA-2G9 also have good affinity for the CSG molecule. None of these MoAbs are cross-reactive with epitopes of derivatives of Rapamycin or FK.

TABLE 24

Percent Inhibition of CSA and AM1 MoAbs with CSA, CSG and CSA Derivatives

| Antigen | CSA-1H6 | CSA-2G9 | AM1-2E10 | AM1-7F5 |
| --- | --- | --- | --- | --- |
| I | 100 | 100 | 100 | 100 |
| II | 0 | 23.1 | 12.7 | 16.6 |
| III | 5.5 | 21.9 | 17.8 | 16.6 |
| HSA | 6.0 | 9.4 | 15.4 | 13.6 |
| CSA | 100 | 100 | 90.4 | 77.5 |
| CSG | 88.6 | 89.8 | 61.2 | 28.8 |

Inhibiting Derivatives:

| Species Identification | Modification |
| --- | --- |
| I | CSA - deuterated on #1 amino acid |
| II | Rapamycin - deuterated and methylated on #7 amino acid |
| III | oxime of FK (#22 amino acid) |

This example demonstrates that, using CSA or CSA metabolite conjugates of this invention, antibodies can be elicited which recognize epitopes on the CSA parent molecule, CSG or other derivatives/analogues of CSA.

Example 20

Measuring the Biological Activity of CSA and CSA Metabolites by in vitro Mixed Lymphocyte Reaction (MLR) Assay The MLR assay is useful for identifying CSA metabolites with biological (immunosuppressive) activity and to quantify this activity relative to the immunosuppressive activity of the parent CSA molecule.

An example of a mixed lymphocyte proliferation assay procedure useful for this purpose is presented graphically in FIG. 9 and is performed as follows:

Two-way Mixed Lymphocyte Reaction Assay:
1. Collect blood from two individuals (20 mls each) and isolate lymphocytes using Ficoll-Paque (Pharmacia Biotech).
2. Count lymphocytes at 1:10 dilution in 2% acetic acid (v/v).
3. Prepare 10 mls of each lymphocyte populations (A+B) at $1 \times 10^6$ cells/ml in DMEM/20% FCS (v/v).
4. Set up a 96 well sterile tissue culture plate, flat bottom (Sarstedt, cat #83.1835). To each well add:
5. Aliquot 100 µl per well lymphocyte population A
6. Aliquot 100 µl per well lymphocyte population B
7. Aliquot 20 µl per well of drug (CSA and CSA metabolites) at 0, 2.5, 5, 10, 25, 50 and 100 µg/L in triplicate in DMEM with no supplements.
8. To measure the effect of drug on proliferation, incubate the plate for 5 days at 37° C. in 5 % $CO_2$ atmosphere.
9. On day 6, prepare 3.2 mls of 1:50 dilution of Methyl-$^3$H-Thymidine (Amersham Life Science, cat # TRK 120) in DMEM with no supplements. Add 30 µl per well and incubate for 18 hours at 37° C. in 5% $CO_2$ atmosphere.
10. On day 7 cells are harvested onto glass microfiber filters GF/A (Whatman, cat #1820024) using a Cell-Harvestor (Skatron, cat #11019). Wash cells 3× with 1.0-ml sterile distilled water.

Note: All procedures are done using sterile techniques in a biological flow hood.

11. Place filters in Scintillation vials and add 1.5 mls of SciniSafe Plus 50% scintillation fluid (Fisher, cat # SX-25-5).
12. Measure the amount of radioactivity incorporated in the lymphocytes using a beta counter (Micromedic System Inc., TAURUS Automatic Liquid Scintillation Counter) for 1.0 minute.
13. Calculate averages and standard deviations for each drug and express results as:

$$\%Inhibition = 1 - \left[\frac{Ave\ CPM\ of\ test\ drug}{Ave\ CPM\ of\ zero\ drug}\right] \times 100$$

% Proliferation=100–% Inhibition

Other mixed lymphocyte reaction assays known in the art can also be used.

The MLR assay can be utilized to select antibodies of the invention which bind biologically active CSA metabolites and/or the parent CSA molecule. Antibodies could also be selected for reactivity to biologically inactive metabolite moieties. Examples of MoAbs displaying such reactivity/selectivity are shown in Table 25.

TABLE 25

Ability of Anti-CSA Metabolite MoAbs to Block CSA Inhibition of MLR

| Purified MoAbs | % Inhibition of MLR |
| --- | --- |
| Media Control (no CSA, no MoAbs) | 0 |
| CSA 100 ug/L (no MoAbs) | 49.1 |
| AM1-3A6 | 3.6 |
| AM1-7F5 | 0 |
| AM9-1-7D2 | 5 |
| AM9-1-2A11 | 46.7 |
| AM9-9-6C3 | 0 |
| AM9-9-11G9 | 0 |
| AM19-1-7E12 | 0 |
| AM19-1-4E8 | 0 |
| AM19-9-1D8 | 0 |
| AM19-9-5A6 | 41.5 |
| AM19-9-1E11 | 0 |
| AM19-9-2G9 | 42.5 |

As shown in Table 25, a 100 ug/L concentration of CSA inhibited MLR by 49.1% (the $IC_{50}$ value), media alone caused no inhibition of MLR. A number of MoAbs blocked the CSA inhibition of MLR, indicating MoAb binding (or cross-reactivity) to epitopes of the CSA molecule. All MoAbs were control tested in this MLR assay (with no CSA drug) to determine non-specific suppressive effects. No MoAbs showed any suppression of MLR. Three MoAbs (AM9-1-2A11; AM19-9-5A6; AM19-9-2G9) showed no ability to block CSA inhibition of MLR. This result confirms the inhibition ELISA results which demonstrate selectivity to metabolite moieties. AM9-1-2A11 is selective for AM1 and AM1c; AM19-9-5A6 is selective for AM1; and AM19-9-2G9 for AM1 and AM9. These MoAbs do not bind or cross-react with epitopes of the CSA molecule.

Example 21

Immunoassay Kits Using Polyclonal and Monoclonal Antibodies to Specific Sites of Cyclosporine The polyclonal and monoclonal antibodies to specific sites of CSA of the invention may be used for development of immunoassays or TDM kits. Such assays could include, but are not limited to, direct, inhibition, competitive or sandwich immunoassays (ELISA or other assay systems), RIA, solid or liquid phase assays or automated assay systems.

In an automated assay format, the CSA-2G9 MoAb can significantly inhibit a CSA- enzyme conjugate (27.6%; maximal inhibition in this assay format is 30%). This inhibition can be modulated (blocked) by free CSA. Other MoAbs elicited using conjugates of this invention which can be optimized for CSA quantification in automated TDM assays, include (but not limited to) MoAbs CSA-1H6; AM1-7F5 produced by the hybridoma cell line deposited with ATCC as designation PTA-4142 on Mar. 13, 2002; AM1-3B1 produced by the hybridoma cell line deposited with ATCC as designation PTA-4154 on Mar. 30, 2002; AM1-2E10 produced by the hybridoma cell line deposited with ATCC as designation PTA-4141 on Mar. 13, 2002; AM9-1-3C1 produced by the hybridoma cell line deposited with ATCC as designation PTA-4155 on Mar. 30, 2002; AM19-1-5D2 produced by the hybridoma cell line deposited with ATCC as designation PTA-4163 on Mar. 30, 2002; AM19-1-4E8; AM19-1-5B3 produced by the hybridoma cell line deposited with ATCC as designation PTA-4147 on Mar. 13, 2002; AM9-9-11H 11 produced by the hybridoma cell line deposited with ATCC as designation PTA-4159 on Mar. 30, 2002 and AM9-9-4F5 produced by the hybridoma cell line deposited with ATCC as designation PTA-4145 on Mar. 13, 2002.

A further aspect of the invention is to use metabolite, selective MoAbs to mop-up or block metabolites in patient samples; thereby reducing anti-CSA metabolite cross-reactivity. This would allow for more accurate determination of levels of the parent CSA molecule in samples. MoAbs of this invention most preferred for this purpose include, but not limited to, MoAbs AM1-2E10 produced by the hybridoma cell line deposited with ATCC as designation PTA-4141 on Mar. 13, 2002; AM19-9-5A6 produced by the hybridoma cell line deposited with ATCC as designation PTA 4150 on Mar. 13, 2002; AM9-1-6D4 produced by the hybridoma cell line deposited with ATCC as designation PTA-4157 on Mar. 30, 2002; AM9-1-7D2 produced by the hybridoma cell line deposited with ATCC as designation PTA-4144 on Mar. 13, 2002; AM9-9-11G9 produced by the hybridoma cell line deposited with ATCC as designation PTA-4158 on Mar. 30, 2002; AM9-9-6C3 produced by the hybridoma cell line deposited with ATCC as designation PTA-4146 on Mar. 13, 2002; AM1-3A6; AM19-1-7E12 produced by the hybridoma cell line deposited with ATCC as designation PTA-4161 on Mar. 30, 2002; AM9-1-2A11 produced by the hybridoma cell line deposited with ATCC as designation PTA-4143 on Mar. 13, 2002; AM19-1-1E11 produced by the hybridoma cell line deposited with ATCC as designation PTA-4149 on Mar. 13, 2002; AM19-9-1D8 produced by the hybridoma cell line deposited with ATCC as designation PTA-4148 on Mar. 13, 2002; AM19-9-2G9 produced by the hybridoma cell line deposited with ATCC as designation PTA-4160 on Mar. 30, 2002; and AM9-1-4D6 produced by the hybridoma cell line deposited with ATCC as designation PTA4156 on Mar. 30, 2002.

Another aspect of this invention is that CSA or metabolite hapten conjugates can be used to prepare antibodies to CSA epitopes outside the region of a.a. #1. Other antibodies can be prepared to CSA epitopes outside the region of the a.a. #9. Using antibodies from two different species, sandwich assays for TDM can be developed. For example, mouse polyclonal or monoclonal antibodies (Ab A) prepared with the AM9-9-DVS hapten conjugate would bind CSA; rabbit polyclonal or monoclonal antibodies (Ab B) prepared with CSA-DVS or AM1-DVS hapten would bind epitopes on the other face of the CSA molecule to provide a sandwich assay. This invention also provides methods to prepare polyclonal or monoclonal antibodies to various epitopes of CSA metabolites. Methods to block, bind or remove specific metabolites with these MoAbs can be developed using methods known in the art.

TDM assays may also be designed to measure levels of the CSA parent molecule and certain biologically active and/or toxic metabolites using combinations of MoAbs. For example, a combination of a MoAb (specific for the parent CSA molecule), with a MoAb (specific for AM1 and AM1c metabolites), and a MoAb (specific for AM9 metabolite) could be used to measure CSA, AM1, AM1c and AM9 metabolite levels. Such MoAbs could also be used alone to quantify levels of CSA or specific CSA metabolites.

The examples disclosed in this application demonstrate the preparation of polyclonal-and monoclonal antibodies useful in TDM assays to measure parent CSA/CSA derivative levels; or parent CSA/CSA derivative and all CSA metabolite levels, or parent CSA/CSA derivative and specific metabolite levels (i.e., AM1 and/or AM1c and/or AM9), or for the development of TDM assays to measure specific CSA metabolite levels. This invention is not limited to production of monoclonal antibodies using immunogens described in Examples 2–5, as these are presented merely as proof of principle of the invention. This invention also encompasses the preparation of immunogens using CSA derivatives or any CSA metabolites and the production of polyclonal and monoclonal antibodies to all CSA metabolites (i.e., phase I, II , etc. metabolites).

Upon reading the present disclosure, modifications of the invention will be apparent to one skilled in the art. These modifications are intended to be encompassed by the present disclosures, Examples and the claims appended hereto.

What is claimed is:

1. An isolated antibody selected from the group consisting of CSA-2G9 produced by the hybridoma cell line deposited with ATCC as PTA-4170, AM1-7F5 produced by the hybridoma cell line deposited with ATCC as PTA-4142, AM1-3B1 produced by the hybridoma cell line deposited with ATCC as PTA-4154, AM1-2E10 produced by the hybridoma cell line deposited with ATCC as PTA-4141, AM9-1-3C1 produced by the hybridoma cell line deposited with ATCC as PTA-4155, AM19-1-5D2 produced by the hybridoma cell line deposited with ATCC as PTA-4163, AM19-1-5B3 produced by the hybridoma cell line deposited with ATCC as PTA-4147, AM19-9-5A6 produced by the hybridoma cell line deposited with ATCC as PTA-4150, AM9-1-6D4 produced by the hybridoma cell line deposited with ATCC as PTA-4157, AM9-1-7D2 produced by the hybridoma cell line deposited with ATCC as PTA-4144, AM9-9-11G9 produced by the hybridoma cell line deposited with ATCC as PTA-4158, AM9-9-6C3 produced by the hybridoma cell line deposited with ATCC as PTA-4146, AM19-1-7E12 produced by the hybridoma cell line deposited with ATCC as PTA-4161, AM9-1-2A11 produced by the hybridoma cell line deposited with ATCC as PTA-4143, AM19-9-1E11 produced by the hybridoma cell line deposited with ATCC as PTA-4149, AM19-9-1D8 produced by the hybridoma cell line deposited with ATCC as PTA-4148, AM19-9-2G9 produced by the hybridoma cell line deposited with ATCC as PTA-4160, AM9-9-11H11 produced by the hybridoma cell line deposited with ATCC as PTA-4159, AM9-9-4F5 produced by the hybridoma cell line deposited with ATCC as PTA-4145, and AM9-1-4D6 produced by the hybridoma cell line deposited with ATCC as PTA-4156.

2. A hybridoma cell line selected from the group consisting of the hybridoma cell lines deposited with ATCC as PTA4170, PTA-4142, PTA-4154, PTA-4141, PTA-4155, PTA-4163, PTA-4147, PTA-4150, PTA-4157, PTA-4144, PTA-4158, PTA-4146, PTA-4161, PTA-4143, PTA-4149, PTA-4148, PTA-4160, PTA-4159, PTA-4145, and PTA-4156, respectively.

3. An immunoassay kit comprising the antibody according to claim 1.

\* \* \* \* \*

```
                        SEQUENCE LISTING

<160> NUMBER OF SEQ ID NOS:  7

<210> SEQ ID NO 1
<211> LENGTH: 11
<212> TYPE: PRT
<213> ORGANISM: Tolypocladium inflatum
<220> FEATURE:
<221> NAME/KEY: MOD_RES
<222> LOCATION: (1)
<223> OTHER INFORMATION: Position 1 is xaa wherein xaa =
      N-methyl-(4R)-4-but-2E-en-1-yl-4-methyl-(L)-threonine.
<221> NAME/KEY: MOD_RES
<222> LOCATION: (2)
<223> OTHER INFORMATION: Position 2 is xaa wherein xaa =  Abu which is
      2-Aminobutyric acid.
<221> NAME/KEY: MOD_RES
<222> LOCATION: (3)..(11)
<223> OTHER INFORMATION: Positions 3, 4, 6, 9, 10 and 11 are methylated.
<221> NAME/KEY: MOD_RES
<222> LOCATION: (8)
<223> OTHER INFORMATION: Position 8 is a d-amino acid.

<400> SEQUENCE: 1

Xaa Xaa Gly Leu Val Leu Ala Ala Leu Leu Val
  1               5                  10

<210> SEQ ID NO 2
<211> LENGTH: 11
<212> TYPE: PRT
<213> ORGANISM: Tolypocladium inflatum
<220> FEATURE:
<221> NAME/KEY: MOD_RES
<222> LOCATION: (1)
<223> OTHER INFORMATION: Position 1 is xaa wherein xaa =
      N-methyl-(4R)-4-but-2E-en-1-yl-4-methyl-(L)-threon
      ine.
<221> NAME/KEY: MOD_RES
<222> LOCATION: (1)
<223> OTHER INFORMATION: Position 1 is hydroxylated and cyclized.
<221> NAME/KEY: MOD_RES
<222> LOCATION: (2)
<223> OTHER INFORMATION: Position 2 is xaa wherein xaa =  Abu which is
      2-Aminobutyric acid.
<221> NAME/KEY: MOD_RES
<222> LOCATION: (3)..(11)
<223> OTHER INFORMATION: Positions 3, 4, 6, 9, 10 and 11 are methylated.
<221> NAME/KEY: MOD_RES
<222> LOCATION: (8)
<223> OTHER INFORMATION: Position 8 is a d-amino acid.
<221> NAME/KEY: MOD_RES
<222> LOCATION: (9)
<223> OTHER INFORMATION: Position 9 is hydroxylated.

<400> SEQUENCE: 2

Xaa Xaa Gly Leu Val Leu Ala Ala Leu Leu Val
  1               5                  10

<210> SEQ ID NO 3
<211> LENGTH: 11
<212> TYPE: PRT
<213> ORGANISM: Tolypocladium inflatum
<220> FEATURE:
```

```
<221> NAME/KEY: MOD_RES
<222> LOCATION: (1)
<223> OTHER INFORMATION: Position 1 is xaa wherein xaa =
      N-methyl-(4R)-4-but-2E-en-1-yl-4-methyl-(L)-threon
      ine.
<221> NAME/KEY: MOD_RES
<222> LOCATION: (1)
<223> OTHER INFORMATION: Position 1 is hydroxylated and cyclized.
<221> NAME/KEY: MOD_RES
<222> LOCATION: (2)
<223> OTHER INFORMATION: Position 2 is xaa wherein xaa =  Abu which is
      2-Aminobutyric acid.
<221> NAME/KEY: MOD_RES
<222> LOCATION: (3)..(11)
<223> OTHER INFORMATION: Positions 3, 4, 6, 9, 10 and 11 are methylated.
<221> NAME/KEY: MOD_RES
<222> LOCATION: (8)
<223> OTHER INFORMATION: Position 8 is a d-amino acid.

<400> SEQUENCE: 3

Xaa Xaa Gly Leu Val Leu Ala Ala Leu Leu Val
 1               5                  10

<210> SEQ ID NO 4
<211> LENGTH: 11
<212> TYPE: PRT
<213> ORGANISM: Tolypocladium inflatum
<220> FEATURE:
<221> NAME/KEY: MOD_RES
<222> LOCATION: (1)
<223> OTHER INFORMATION: Position 1 is xaa wherein xaa =
      N-methyl-(4R)-4-but-2E-en-1-yl-4-methyl-(L)-threon
      ine.
<221> NAME/KEY: MOD_RES
<222> LOCATION: (2)
<223> OTHER INFORMATION: Position 2 is xaa wherein xaa =  Abu which is
      2-Aminobutyric acid.
<221> NAME/KEY: MOD_RES
<222> LOCATION: (3)..(11)
<223> OTHER INFORMATION: Positions 3, 4, 6, 9, 10 and 11 are methylated.
<221> NAME/KEY: MOD_RES
<222> LOCATION: (8)
<223> OTHER INFORMATION: Position 8 is a d-amino acid.
<221> NAME/KEY: MOD_RES
<222> LOCATION: (1)..(9)
<223> OTHER INFORMATION: Positions 1 or 9 are hydroxylated.

<400> SEQUENCE: 4

Xaa Xaa Gly Leu Val Leu Ala Ala Leu Leu Val
 1               5                  10

<210> SEQ ID NO 5
<211> LENGTH: 11
<212> TYPE: PRT
<213> ORGANISM: Tolypocladium inflatum
<220> FEATURE:
<221> NAME/KEY: MOD_RES
<222> LOCATION: (1)
<223> OTHER INFORMATION: Position 1 is xaa wherein xaa =
      N-methyl-(4R)-4-but-2E-en-1-yl-4-methyl-(L)-threon
      ine.
<221> NAME/KEY: MOD_RES
<222> LOCATION: (2)
<223> OTHER INFORMATION: Position 2 is xaa wherein xaa =  Abu which is
      2-Aminobutyric acid.
<221> NAME/KEY: MOD_RES
<222> LOCATION: (3)..(11)
<223> OTHER INFORMATION: Positions 3, 4, 6, 9, 10 and 11 are methylated.
<221> NAME/KEY: MOD_RES
<222> LOCATION: (8)
<223> OTHER INFORMATION: Position 8 is a d-amino acid.
<221> NAME/KEY: MOD_RES
<222> LOCATION: (9)
<223> OTHER INFORMATION: Position 9 is hydroxlated.
```

```
<400> SEQUENCE: 5

Xaa Xaa Gly Leu Val Leu Ala Ala Leu Leu Val
 1               5                  10

<210> SEQ ID NO 6
<211> LENGTH: 11
<212> TYPE: PRT
<213> ORGANISM: Tolypocladium inflatum
<220> FEATURE:
<221> NAME/KEY: MOD_RES
<222> LOCATION: (1)
<223> OTHER INFORMATION: Position 1 is xaa wherein xaa =
      N-methyl-(4R)-4-but-2E-en-1-yl-4-methyl-(L)-threon
      ine.
<221> NAME/KEY: MOD_RES
<222> LOCATION: (2)
<223> OTHER INFORMATION: Position 2 is xaa wherein xaa = Abu which is
      2-Aminobutyric acid.
<221> NAME/KEY: MOD_RES
<222> LOCATION: (3)..(11)
<223> OTHER INFORMATION: Positions 3, 4, 6, 9, 10 and 11 are methylated.
<221> NAME/KEY: MOD_RES
<222> LOCATION: (8)
<223> OTHER INFORMATION: Position 8 is a d-amino acid.
<221> NAME/KEY: MOD_RES
<222> LOCATION: (1)..(9)
<223> OTHER INFORMATION: Positions 1 and 9 are hydroxylated.

<400> SEQUENCE: 6

Xaa Xaa Gly Leu Val Leu Ala Ala Leu Leu Val
 1               5                  10

<210> SEQ ID NO 7
<211> LENGTH: 11
<212> TYPE: PRT
<213> ORGANISM: Tolypocladium inflatum
<220> FEATURE:
<221> NAME/KEY: MOD_RES
<222> LOCATION: (1)
<223> OTHER INFORMATION: Position 1 is xaa wherein xaa =
      N-methyl-(4R)-4-but-2E-en-1-yl-4-methyl-(L)-threon
      ine.
<221> NAME/KEY: MOD_RES
<222> LOCATION: (1)
<223> OTHER INFORMATION: Position 1 is hydroxylated.
<221> NAME/KEY: MOD_RES
<222> LOCATION: (2)
<223> OTHER INFORMATION: Position 2 is xaa wherein xaa = Abu which is
      2-Aminobutyric acid.
<221> NAME/KEY: MOD_RES
<222> LOCATION: (3)..(11)
<223> OTHER INFORMATION: Positions 3, 4, 6, 9, 10 and 11 are methylated.
<221> NAME/KEY: MOD_RES
<222> LOCATION: (8)
<223> OTHER INFORMATION: Position 8 is a d-amino acid.

<400> SEQUENCE: 7

Xaa Xaa Gly Leu Val Leu Ala Ala Leu Leu Val
 1               5                  10
```